(12) United States Patent
Iwasaki

(10) Patent No.: US 11,442,291 B2
(45) Date of Patent: Sep. 13, 2022

(54) CONTACT LENS AND DETECTION METHOD

(71) Applicant: Sony Corporation, Tokyo (JP)

(72) Inventor: Masanori Iwasaki, Kanagawa (JP)

(73) Assignee: Sony Corporation, Tokyo (JP)

( * ) Notice: Subject to any disclaimer, the term of this patent is extended or adjusted under 35 U.S.C. 154(b) by 360 days.

(21) Appl. No.: 16/635,755

(22) PCT Filed: Aug. 3, 2018

(86) PCT No.: PCT/JP2018/029296
§ 371 (c)(1),
(2) Date: Jan. 31, 2020

(87) PCT Pub. No.: WO2019/027051
PCT Pub. Date: Feb. 7, 2019

(65) Prior Publication Data
US 2020/0257138 A1    Aug. 13, 2020

(30) Foreign Application Priority Data

Aug. 3, 2017 (JP) .............................. JP2017-150559

(51) Int. Cl.
*G02C 7/04* (2006.01)
*A61B 3/10* (2006.01)
*G01N 1/14* (2006.01)
*G01N 21/78* (2006.01)

(52) U.S. Cl.
CPC .............. *G02C 7/049* (2013.01); *A61B 3/101* (2013.01); *G01N 1/14* (2013.01); *G01N 21/78* (2013.01)

(58) Field of Classification Search
CPC .......... G02C 7/049; A61B 3/101; G01N 1/14; G01N 21/78
See application file for complete search history.

(56) References Cited

U.S. PATENT DOCUMENTS

| | | | |
|---|---|---|---|
| 2002/0049389 A1* | 4/2002 | Abreu ...................... | G02C 7/04 600/318 |
| 2009/0165876 A1* | 7/2009 | Atkin ................... | B01L 3/50273 137/833 |
| 2012/0245444 A1 | 9/2012 | Otis et al. | |

(Continued)

FOREIGN PATENT DOCUMENTS

| | | |
|---|---|---|
| JP | 62-133937 | 6/1987 |
| JP | 2005-502389 | 1/2005 |

(Continued)

OTHER PUBLICATIONS

International Search Report and Written Opinion issued in connection with PCT/JP2018/029296, dated Nov. 6, 2018. (9 pages).

*Primary Examiner* — William R Alexander
*Assistant Examiner* — Sharrief I Broome
(74) *Attorney, Agent, or Firm* — K&L Gates LLP

(57) ABSTRACT

A contact lens according to an embodiment of the present disclosure includes a lens section attachable to an eyeball, and one or a plurality of structure portions provided in the lens section and intended to accumulate tears. This makes it possible to, for example, measure an absorption spectrum of the tears, by emitting light toward the tears accumulated in the one or plurality of structure portions.

20 Claims, 22 Drawing Sheets

(56) References Cited

U.S. PATENT DOCUMENTS

| | | | | |
|---|---|---|---|---|
| 2014/0043588 A1* | 2/2014 | Grant | ...................... | G02C 7/049 |
| | | | | 351/247 |
| 2014/0343387 A1* | 11/2014 | Pugh | ................... | A61B 5/6821 |
| | | | | 600/365 |
| 2015/0164321 A1* | 6/2015 | Weibel | ..................... | A61B 3/16 |
| | | | | 600/405 |
| 2016/0018671 A1* | 1/2016 | Waite | ...................... | A61P 37/08 |
| | | | | 351/159.04 |

FOREIGN PATENT DOCUMENTS

| | | | |
|---|---|---|---|
| JP | 2005-502389 | A | 1/2005 |
| JP | 2007-155674 | | 6/2007 |
| JP | 2007-155674 | A | 6/2007 |
| JP | 2009-516844 | | 4/2009 |
| JP | 2009-516844 | A | 4/2009 |
| JP | 2009-109321 | | 5/2009 |
| JP | 2009-109321 | A | 5/2009 |
| JP | 2013-525763 | A | 6/2013 |
| JP | 2013-525873 | | 6/2013 |
| JP | 2015-203664 | | 11/2015 |
| JP | 2015-203664 | A | 11/2015 |
| JP | 2015203664 | A * | 11/2015 |
| JP | 2016-521377 | | 7/2016 |
| JP | 2016-521377 | A | 7/2016 |
| JP | 2016-525904 | | 9/2016 |
| JP | 2016-525904 | A | 9/2016 |
| WO | 2016/029139 | A1 | 2/2016 |

* cited by examiner

[ FIG. 1 ]
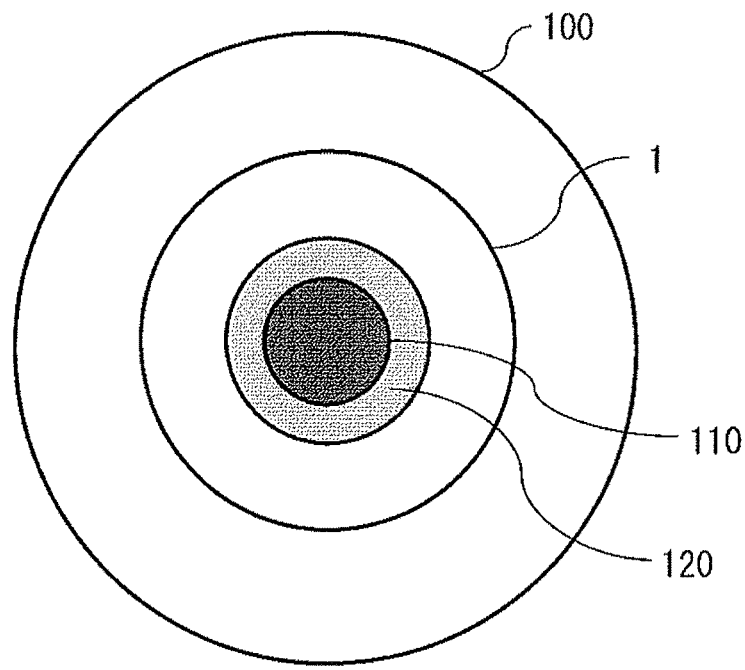
[ FIG. 2 ]
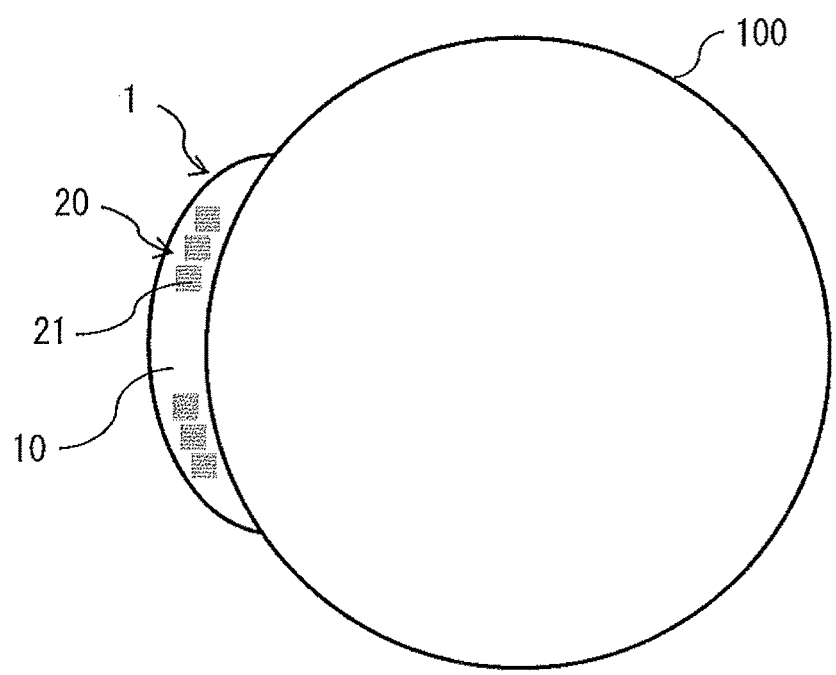

[ FIG. 3A ]
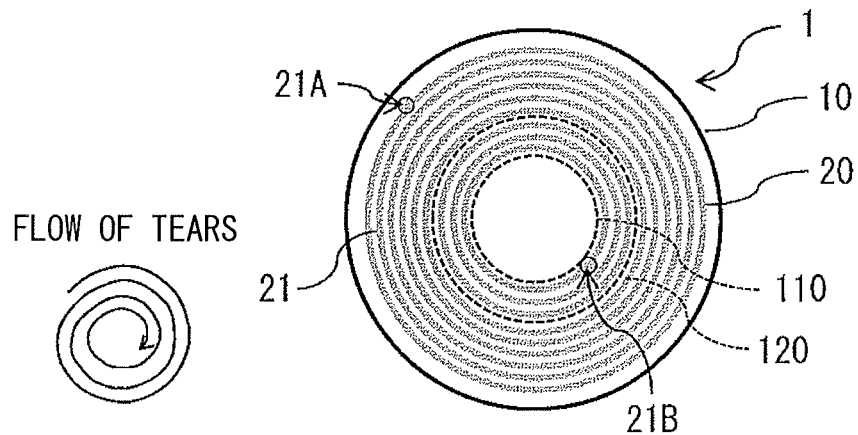
[ FIG. 3B ]
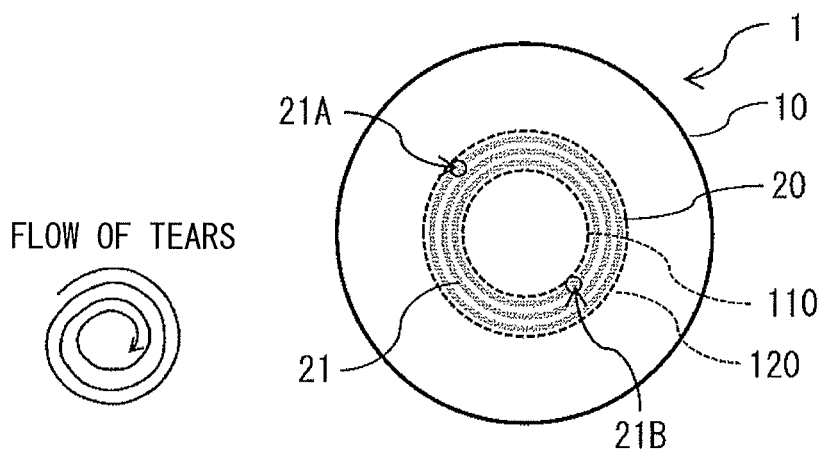
[ FIG. 3C ]
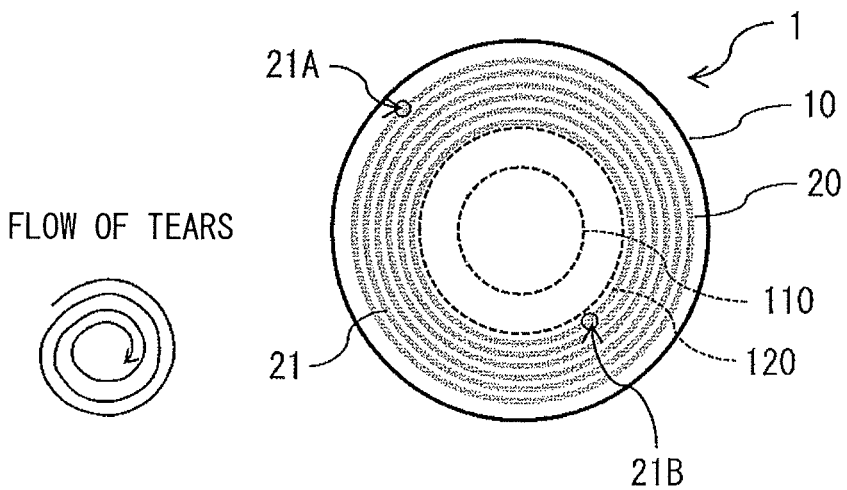

[ FIG. 3D ]
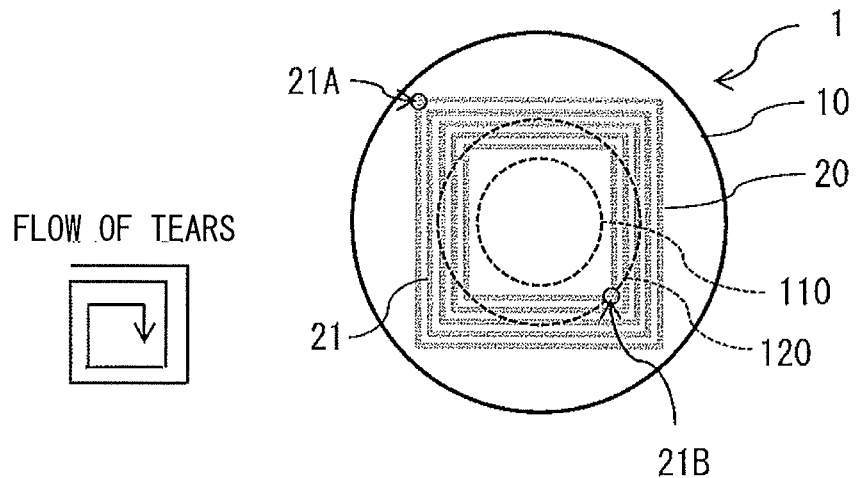
[ FIG. 3E ]
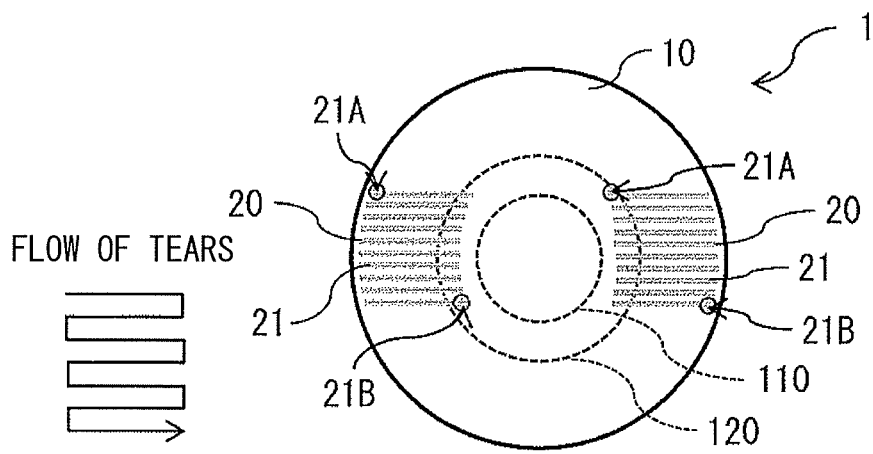
[ FIG. 3F ]
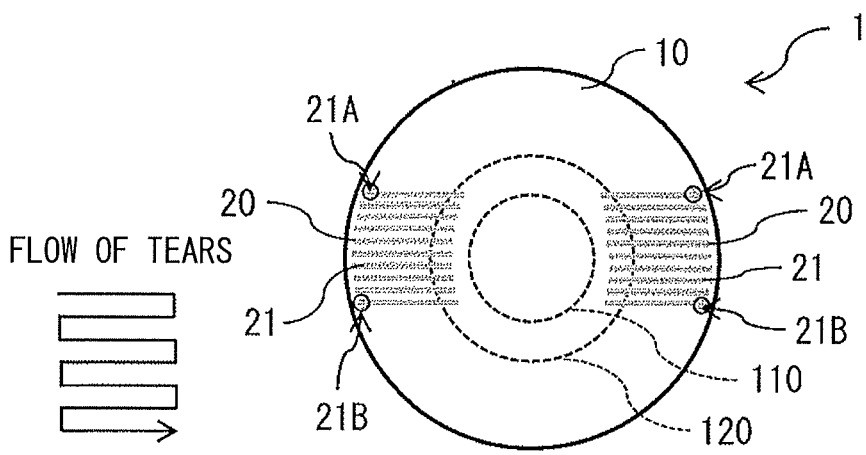

[FIG. 3G]
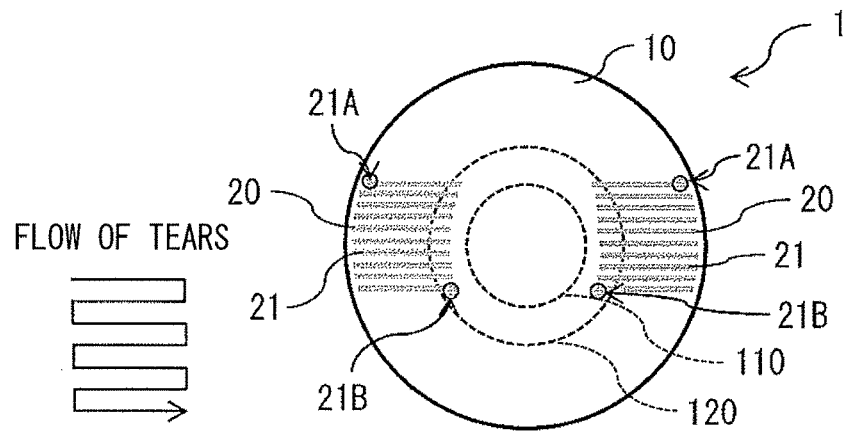
[FIG. 4]
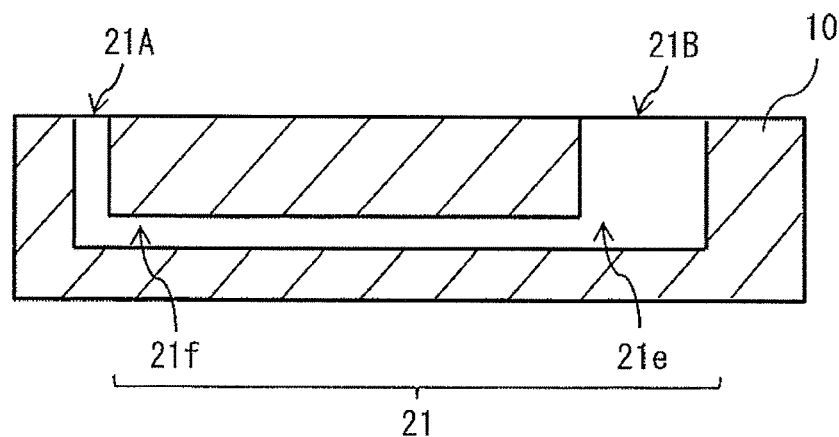
[FIG. 5]
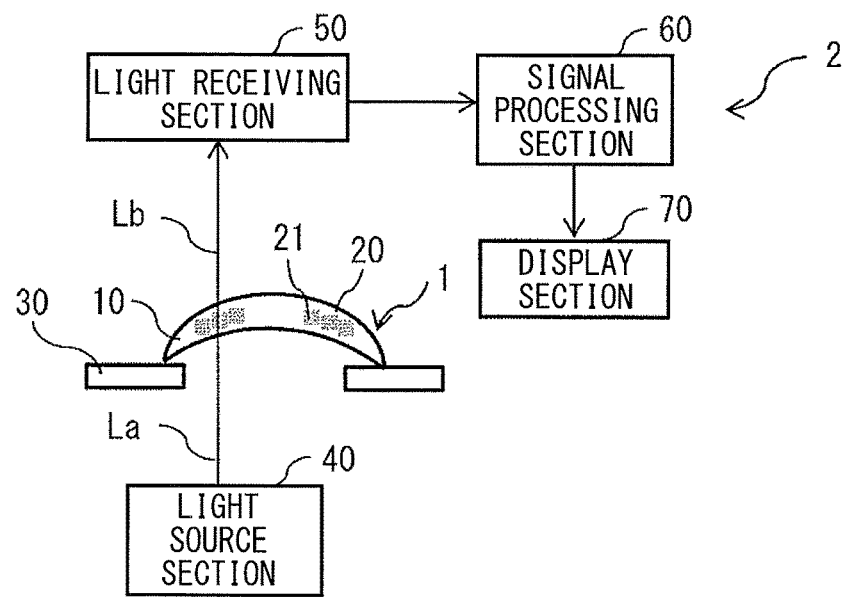

[ FIG. 6 ]
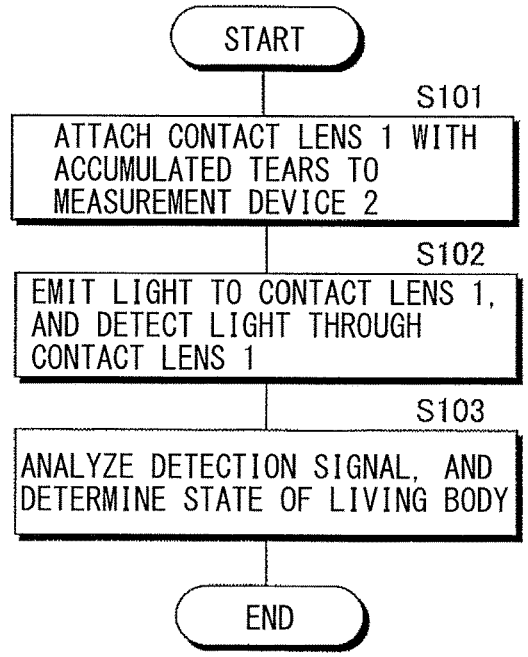
[ FIG. 7 ]
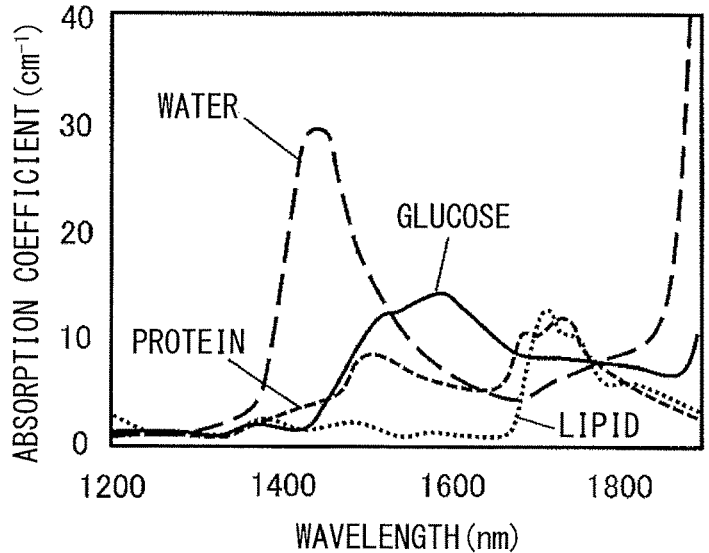
[ FIG. 8 ]
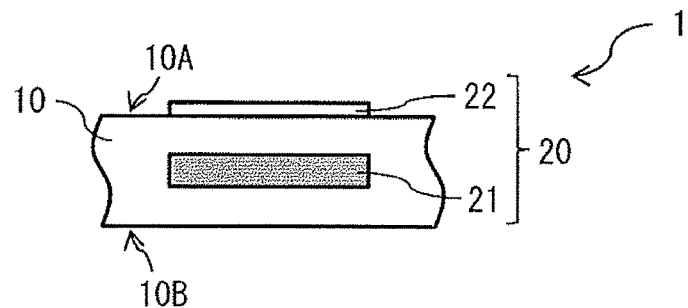

[ FIG. 9 ]
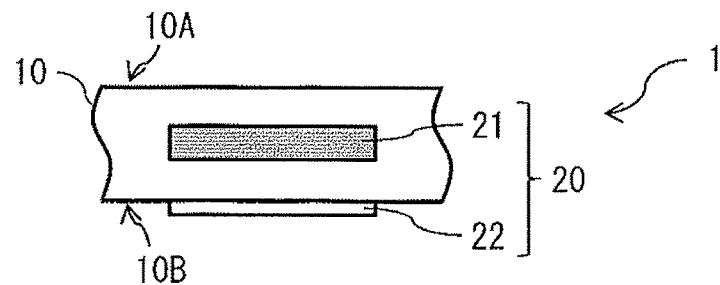
[ FIG. 10 ]
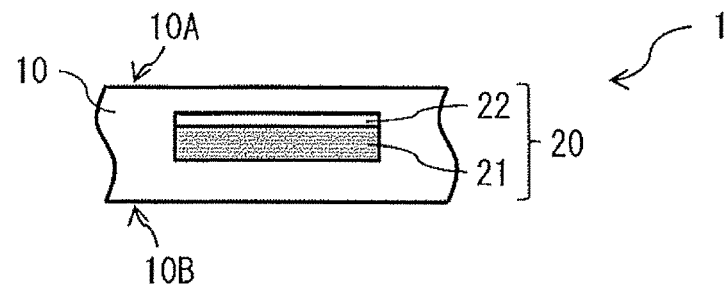
[ FIG. 11 ]
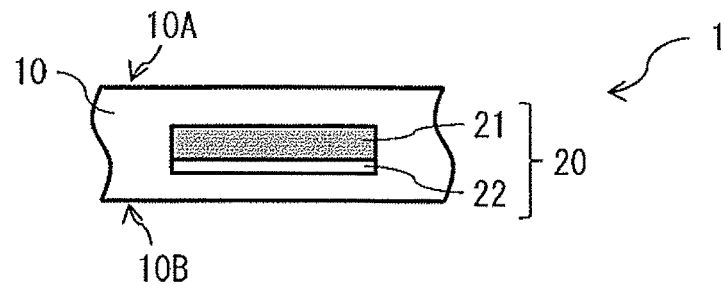
[ FIG. 12 ]
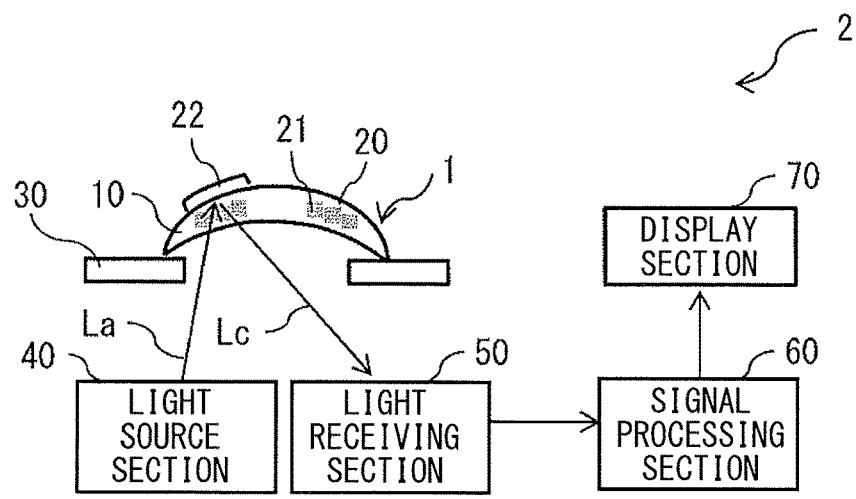

[ FIG. 13 ]
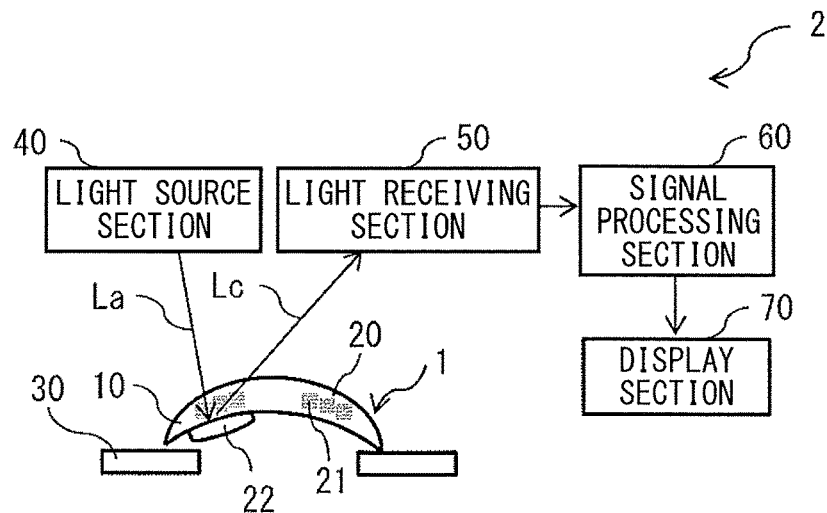
[ FIG. 14 ]
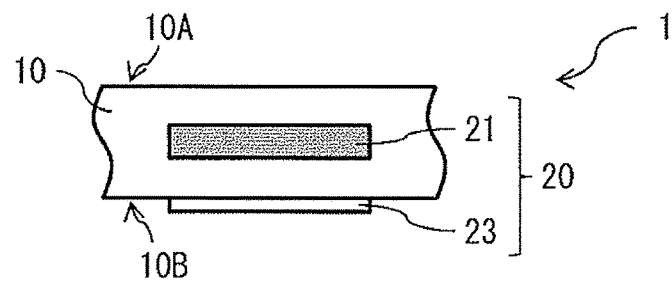
[ FIG. 15 ]
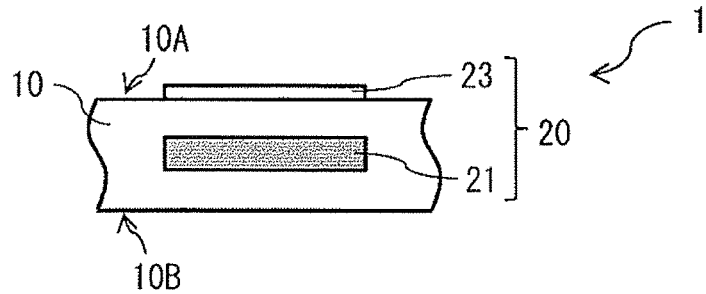
[ FIG. 16 ]
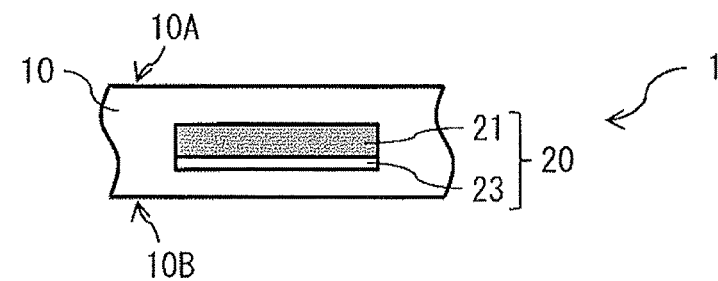

[ FIG. 17 ]
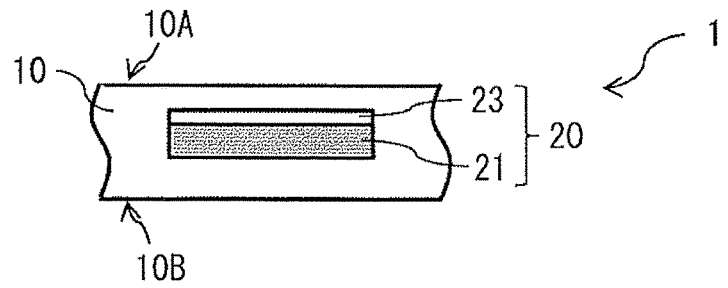
[ FIG. 18 ]
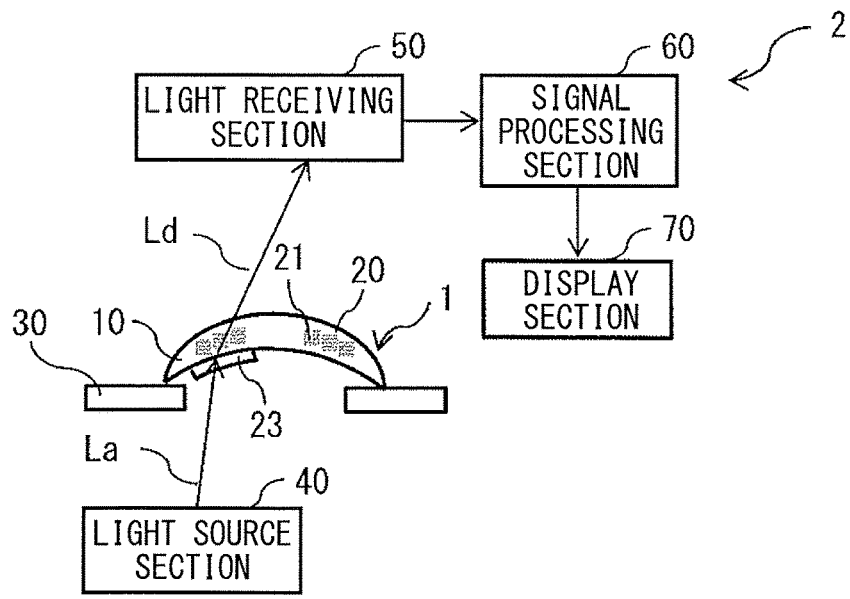
[ FIG. 19 ]
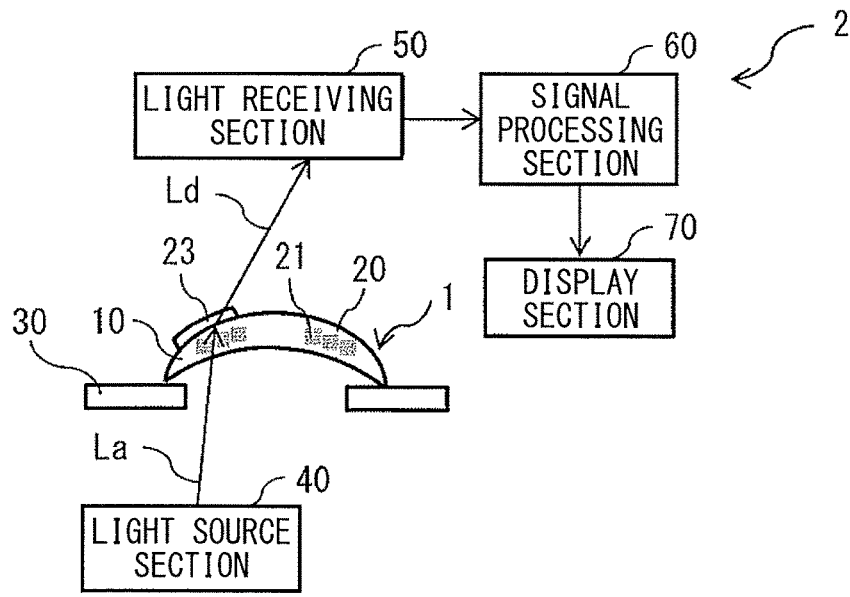

[ FIG. 20 ]
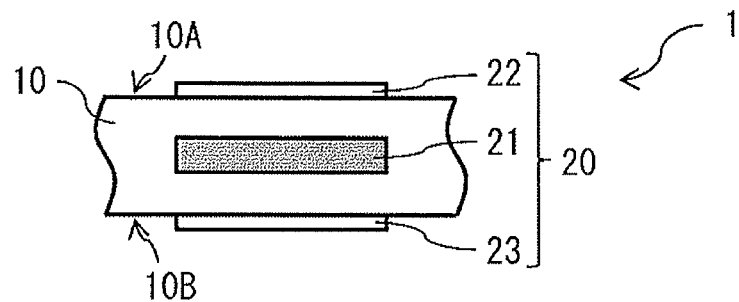
[ FIG. 21 ]
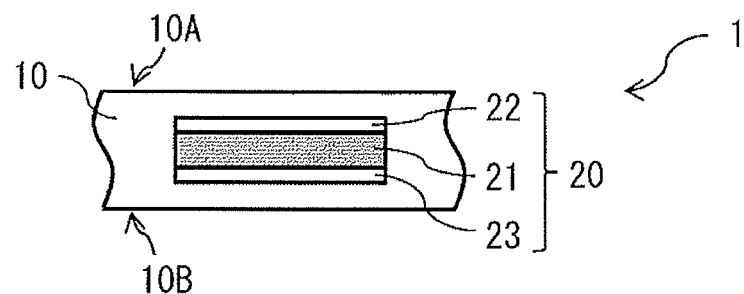
[ FIG. 22 ]
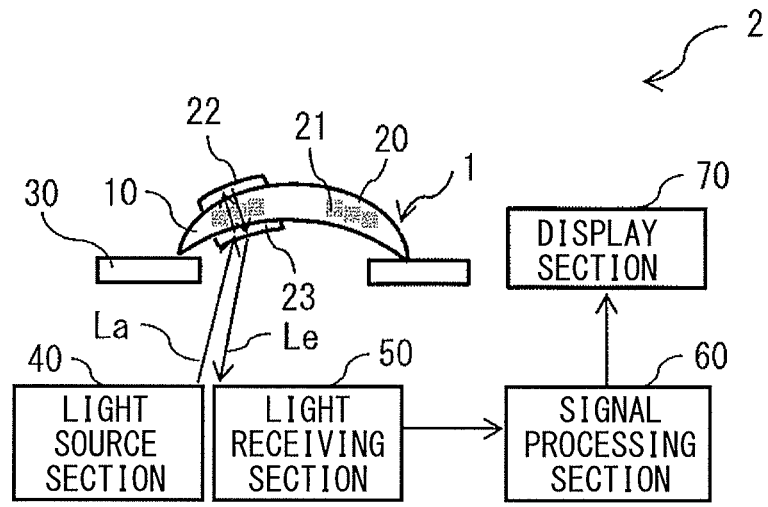
[ FIG. 23 ]
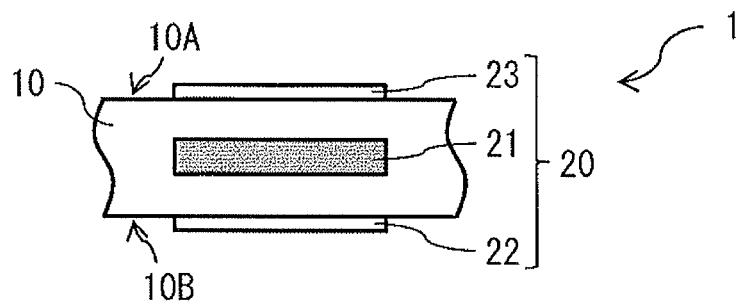

[ FIG. 24 ]
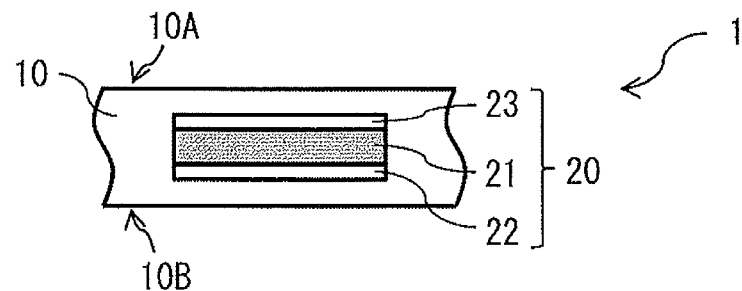
[ FIG. 25 ]
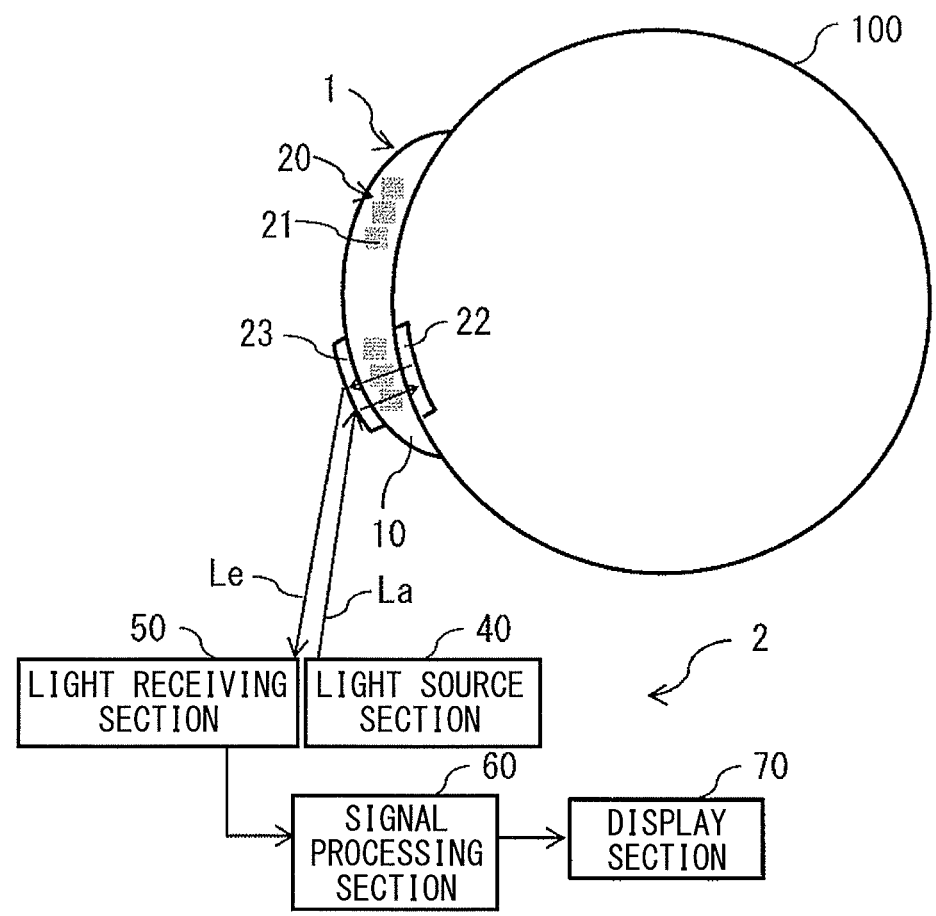

[ FIG. 26 ]
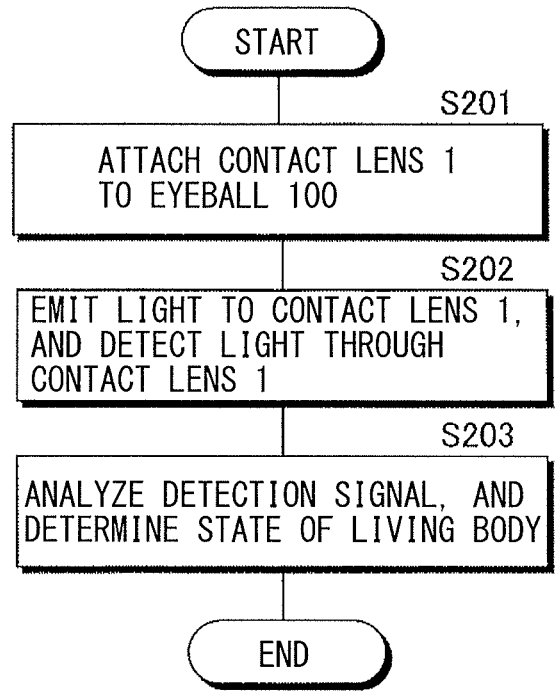
[ FIG. 27 ]
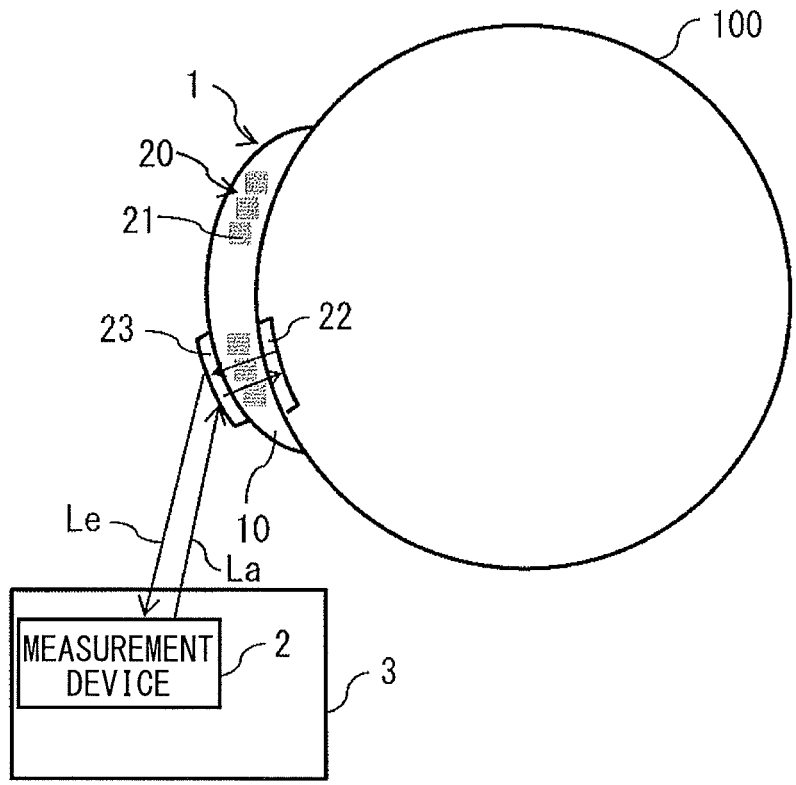

[ FIG. 28 ]
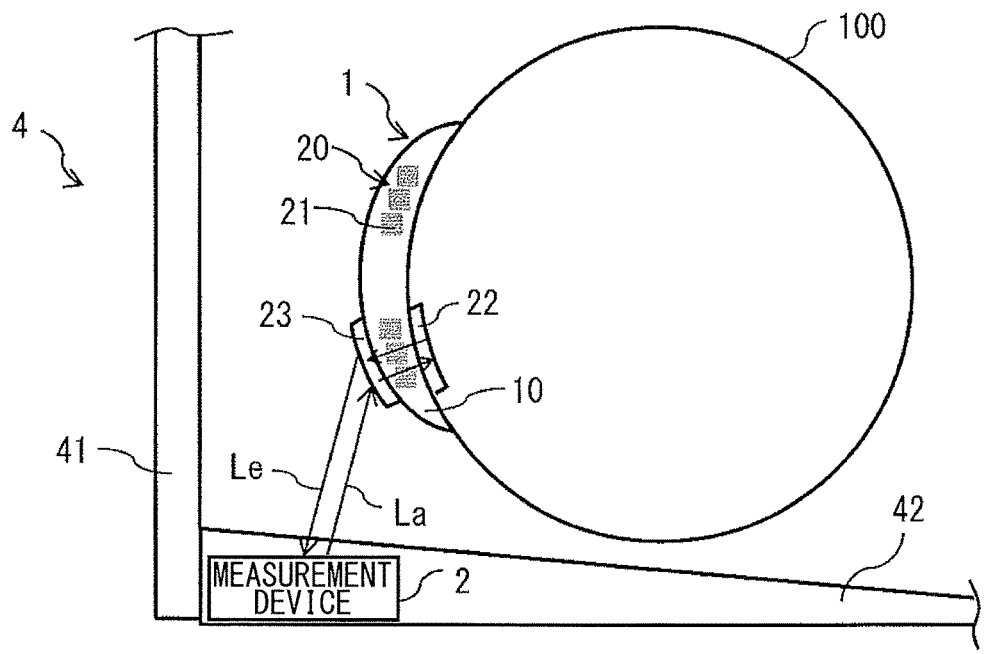
[ FIG. 29 ]
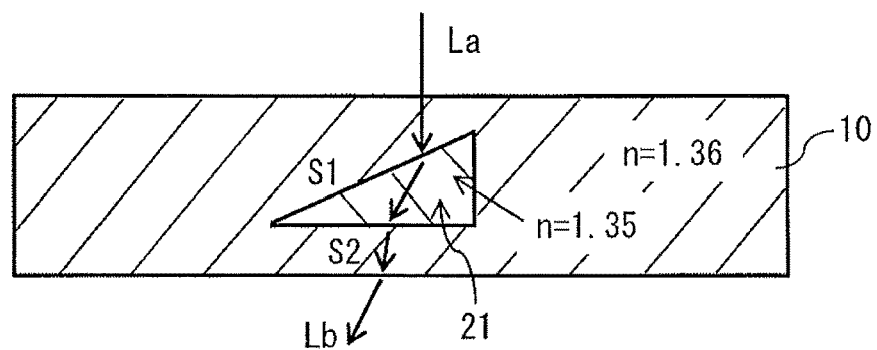
[ FIG. 30 ]
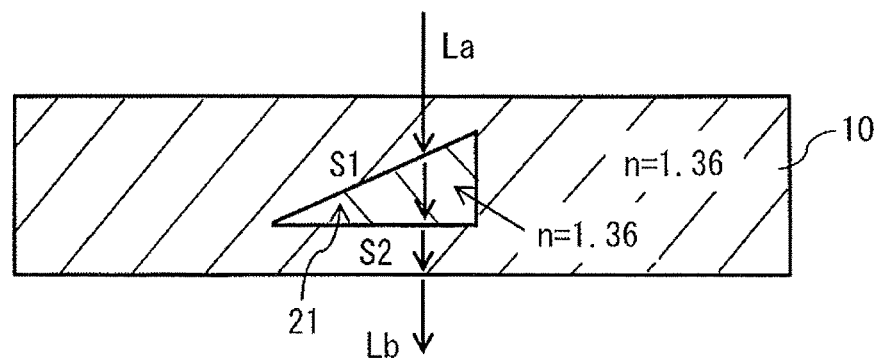

[ FIG. 31 ]
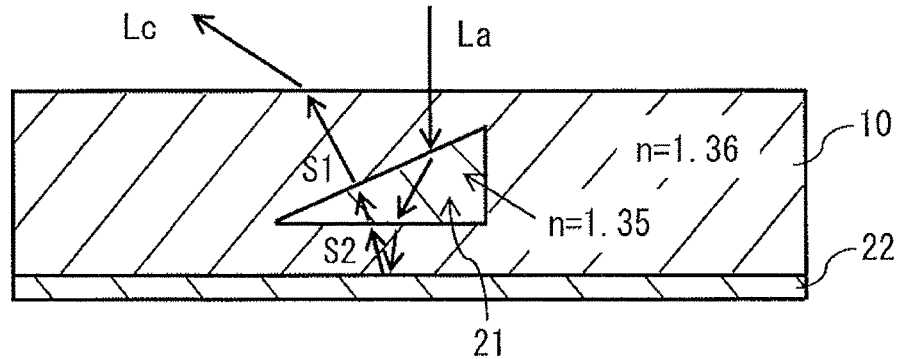
[ FIG. 32 ]
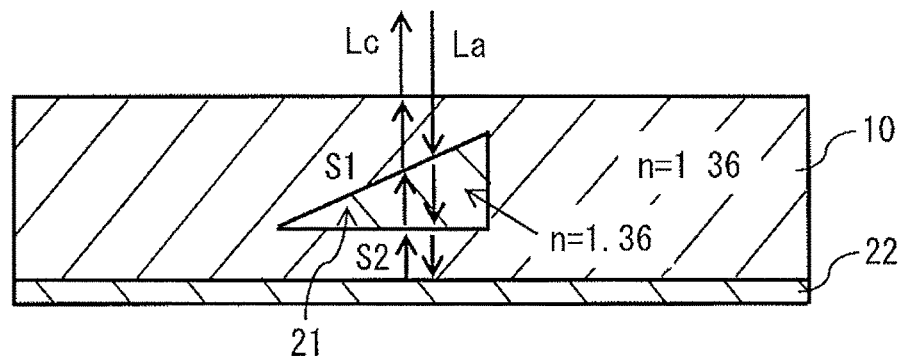
[ FIG. 33 ]
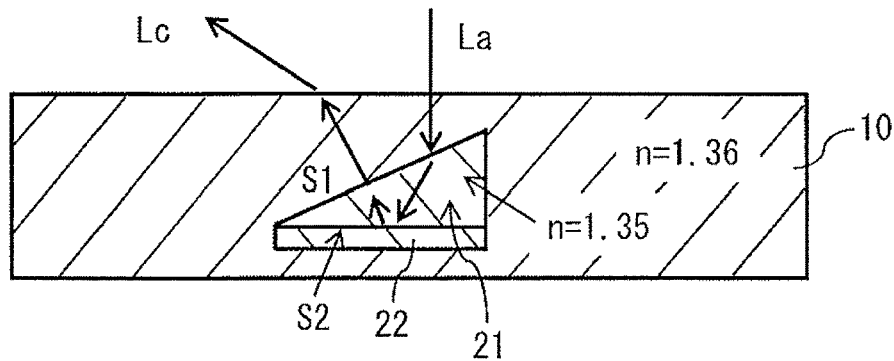
[ FIG. 34 ]
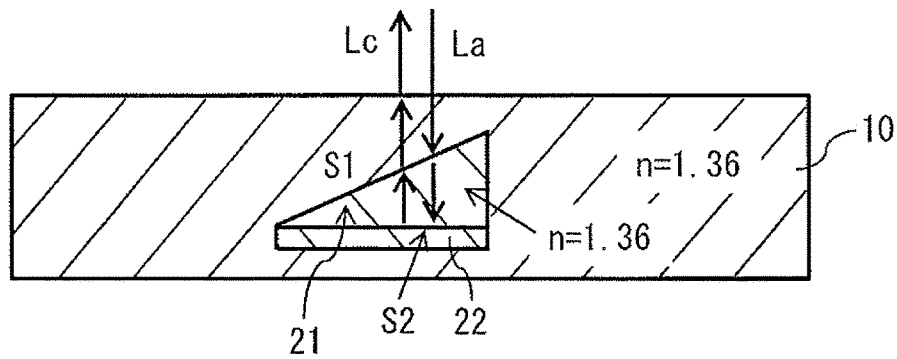

[ FIG. 35 ]
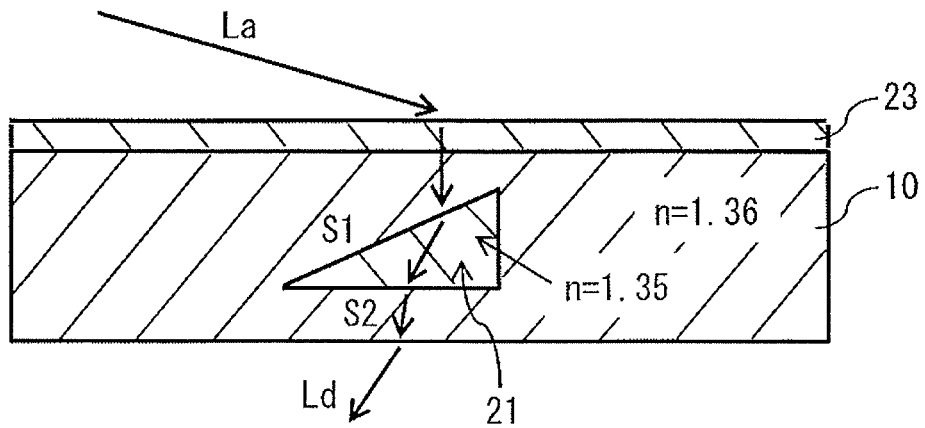
[ FIG. 36 ]
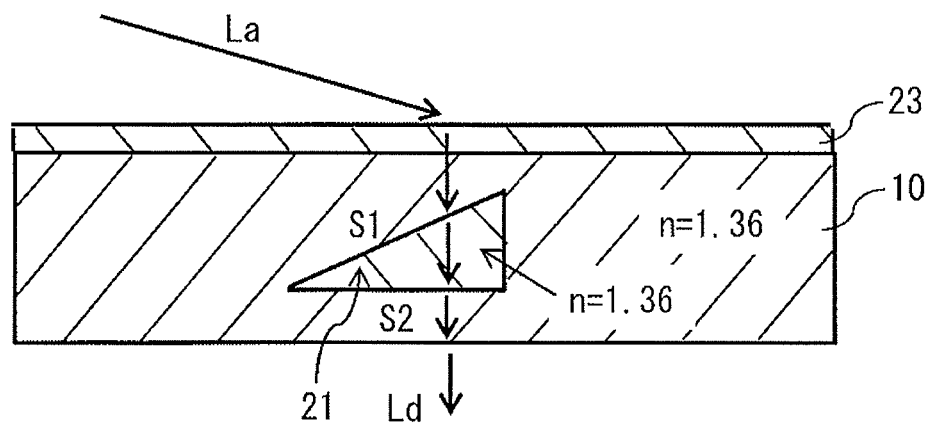
[ FIG. 37 ]
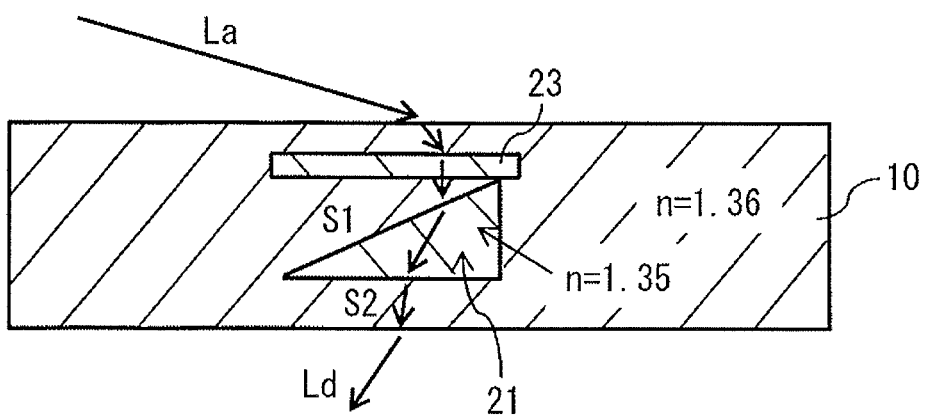

[ FIG. 38 ]
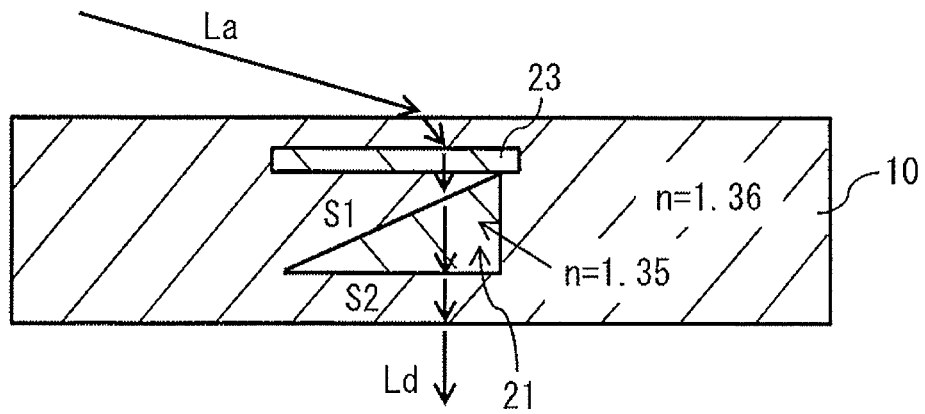
[ FIG. 39 ]
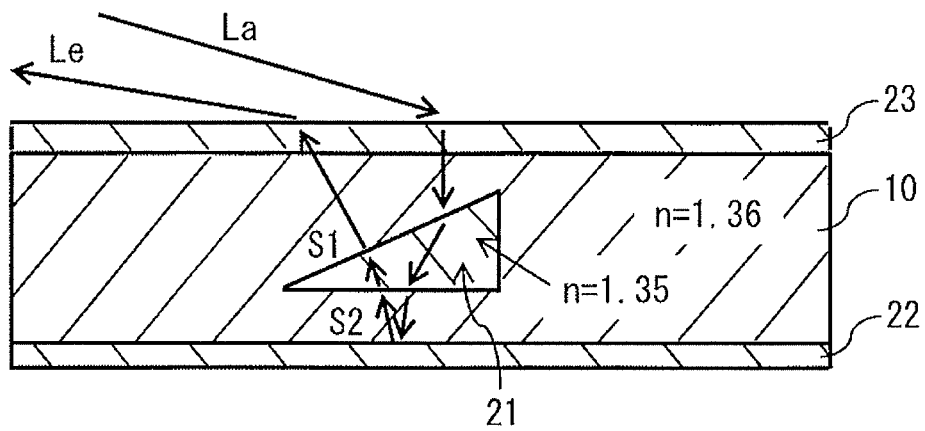
[ FIG. 40 ]
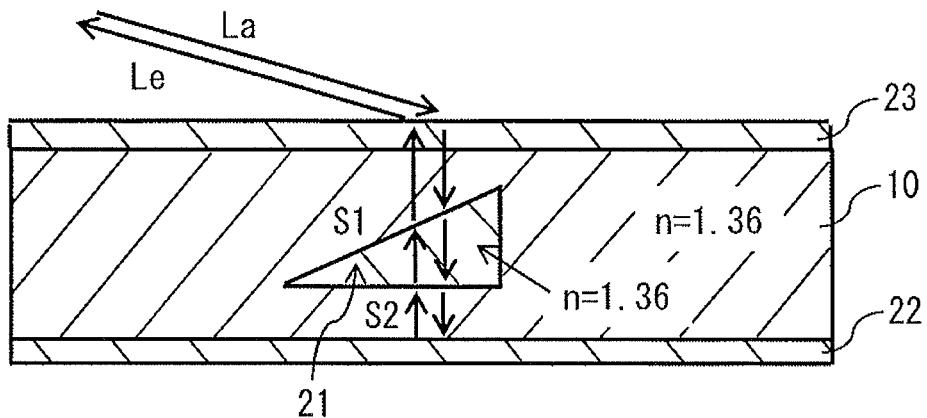

[ FIG. 41 ]
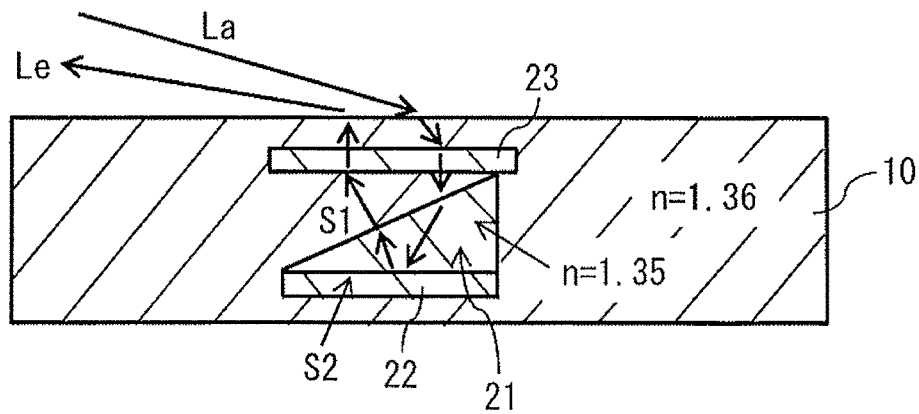
[ FIG. 42 ]
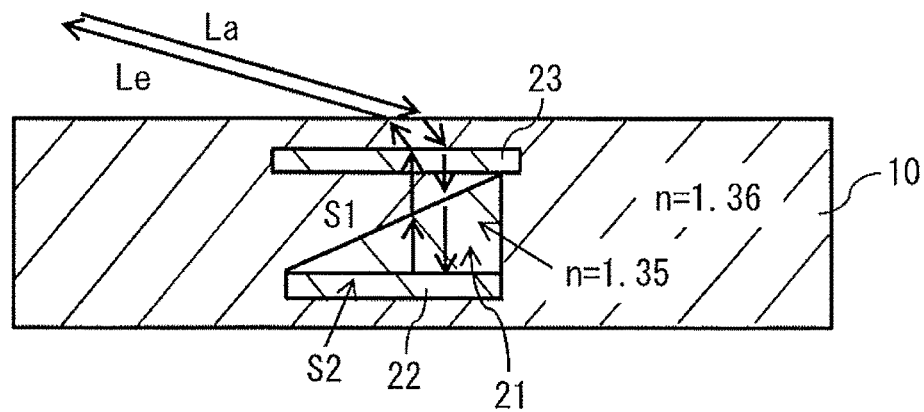
[ FIG. 43 ]
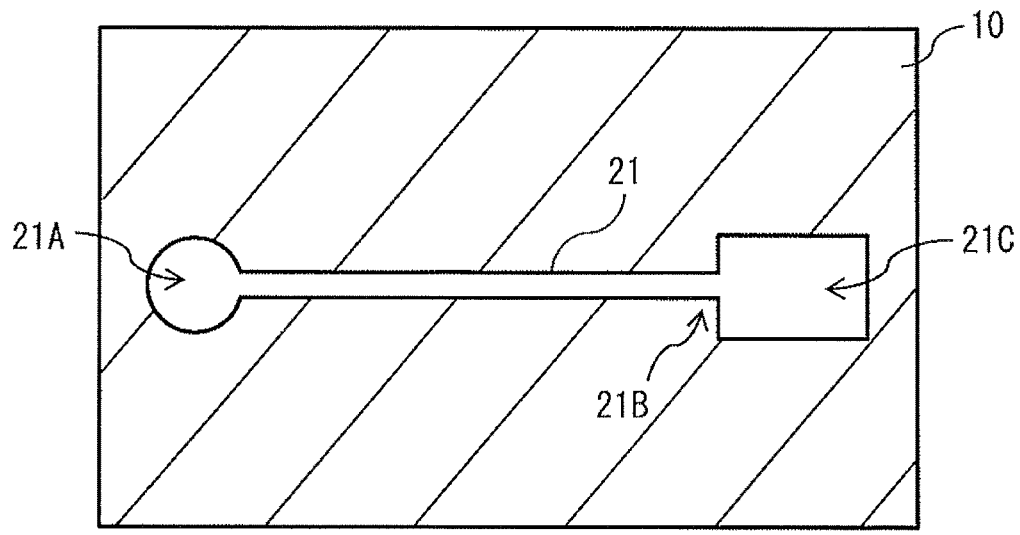

[ FIG. 44 ]
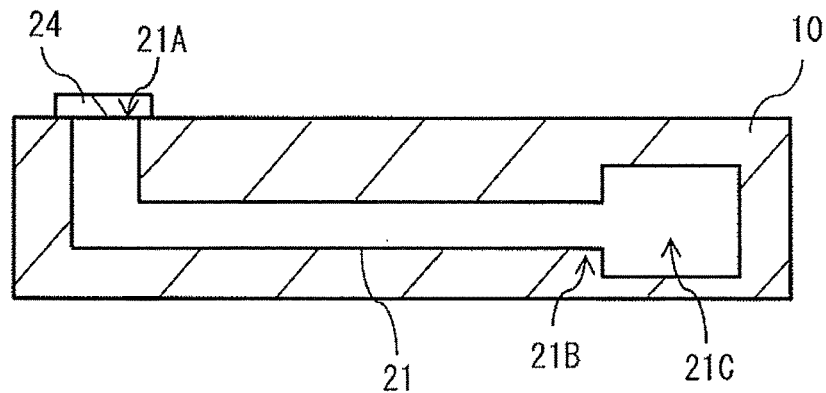
[ FIG. 45 ]
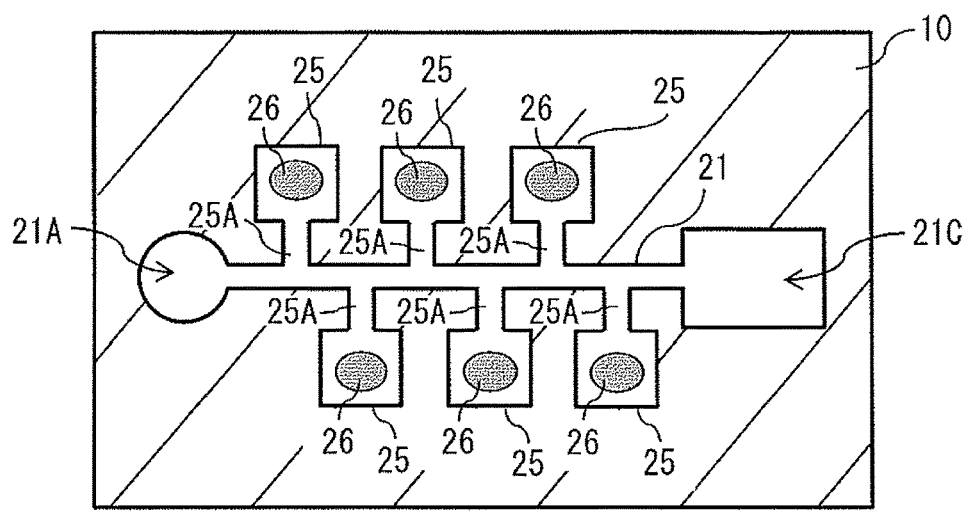
[ FIG. 46 ]
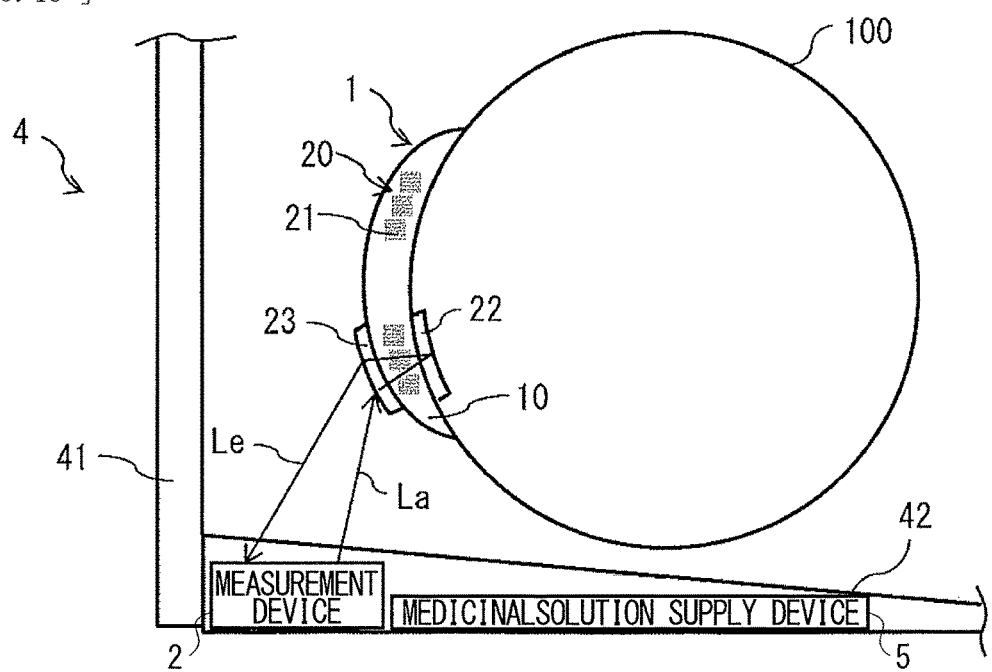

[ FIG. 47 ]
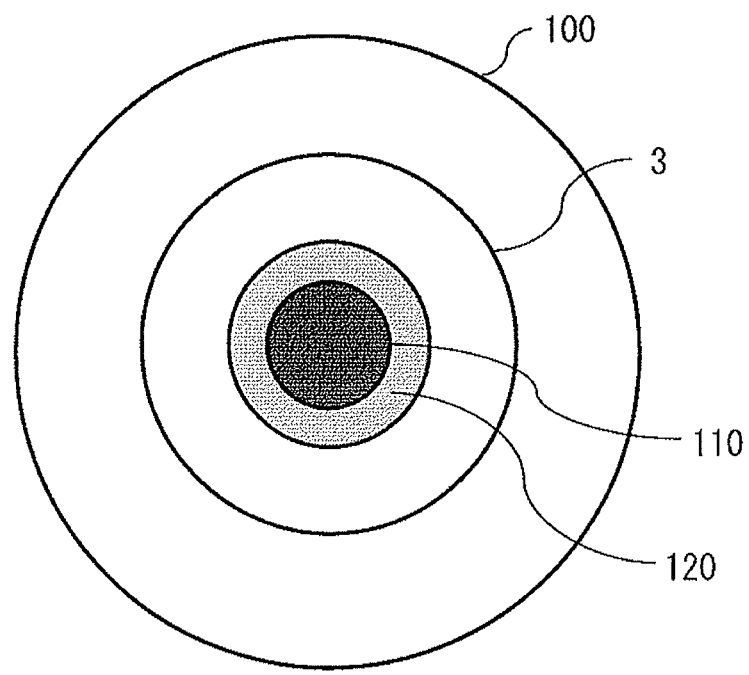
[ FIG. 48 ]
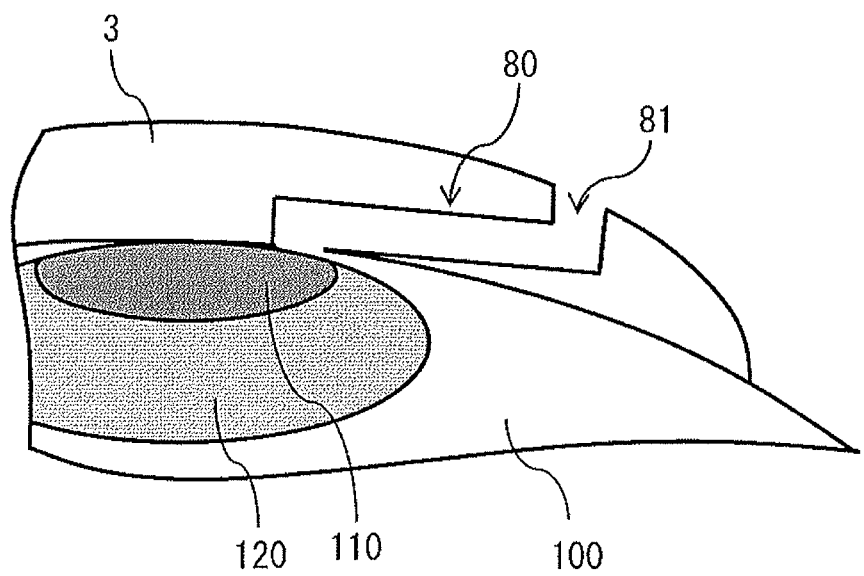

[ FIG. 49 ]
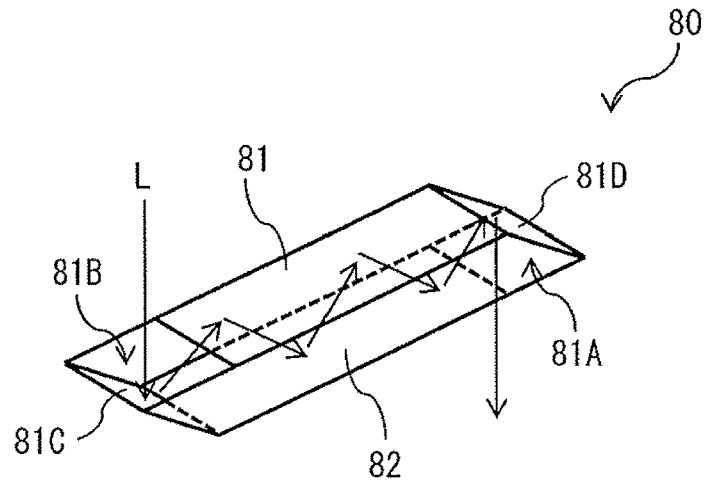
[ FIG. 50 ]
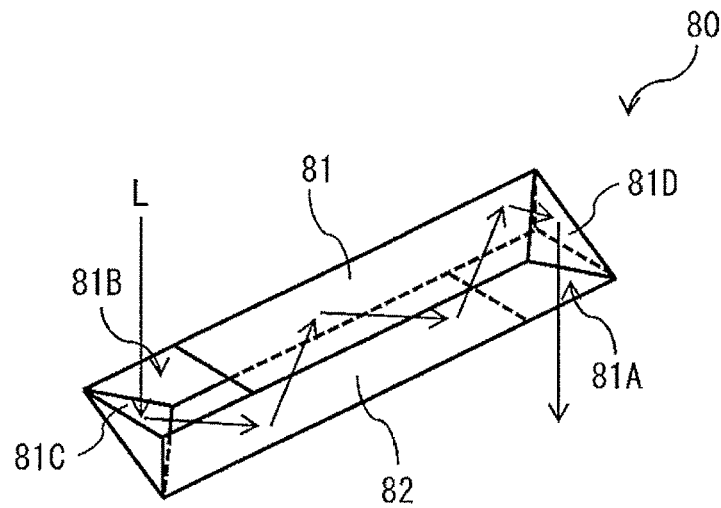
[ FIG. 51 ]
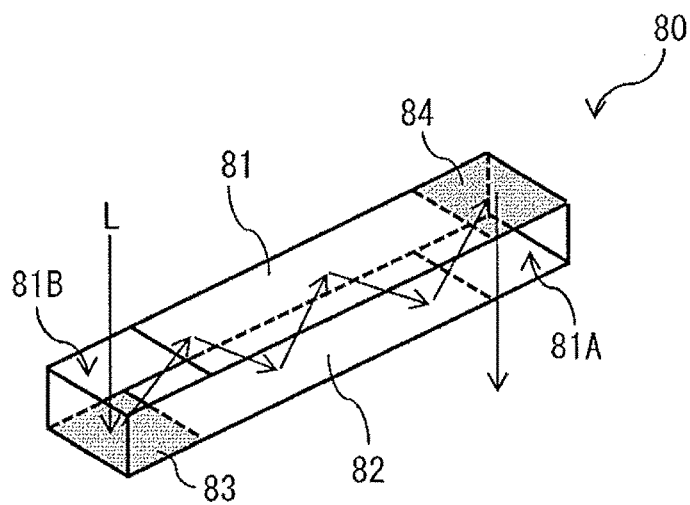

[ FIG. 52 ]
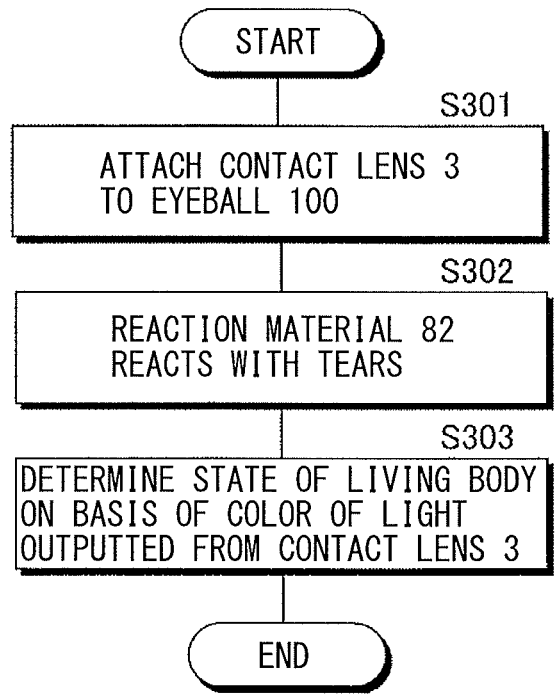
[ FIG. 53 ]
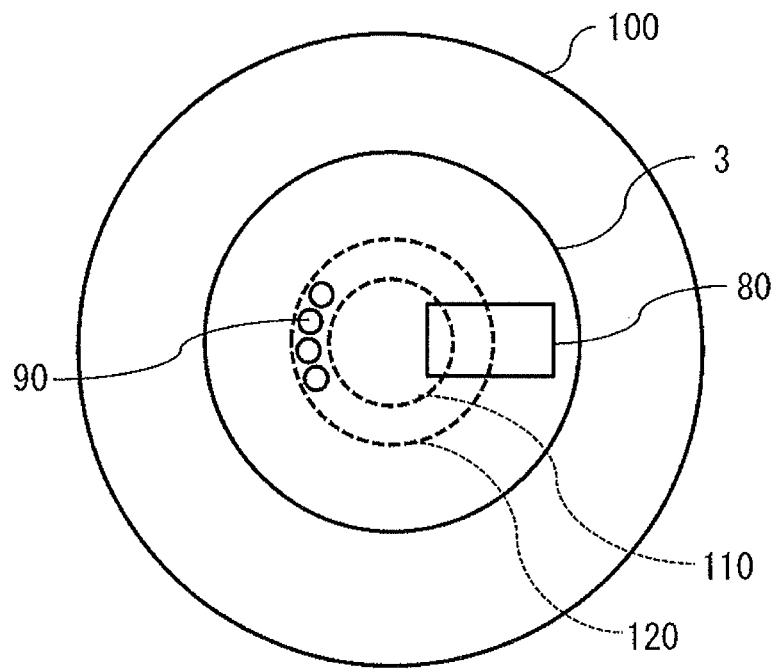

[ FIG. 54 ]
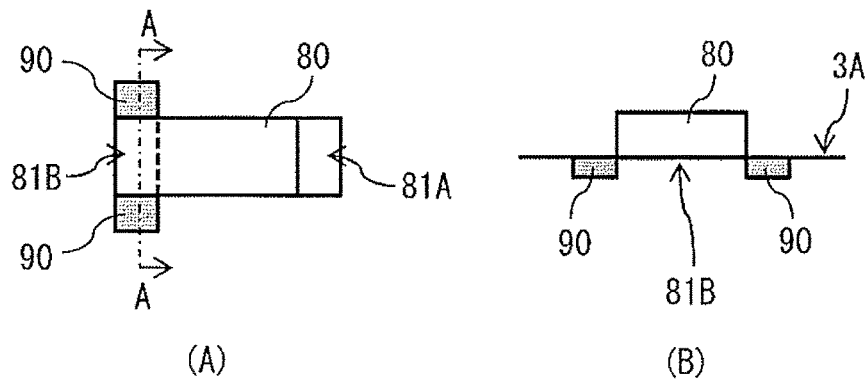
(A)    (B)
[ FIG. 55 ]
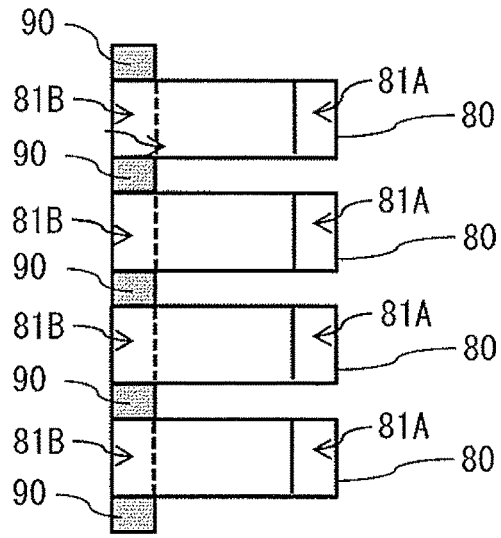
[ FIG. 56 ]
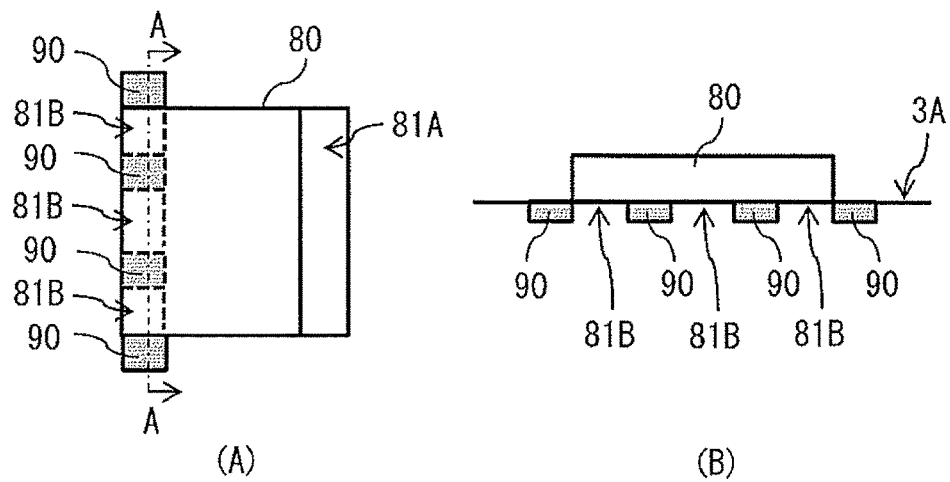
(A)    (B)

[ FIG. 57 ]
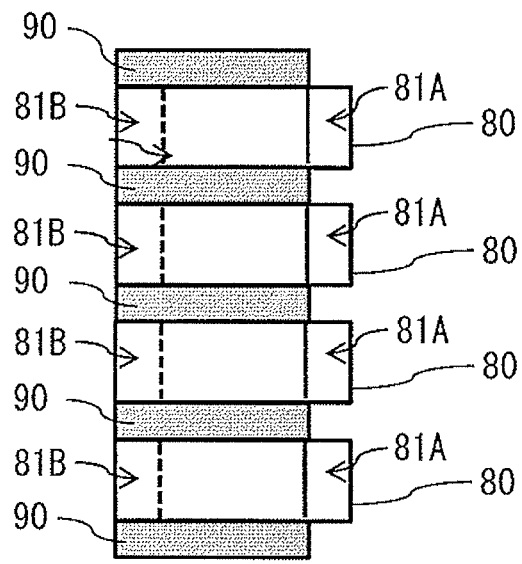
[ FIG. 58 ]
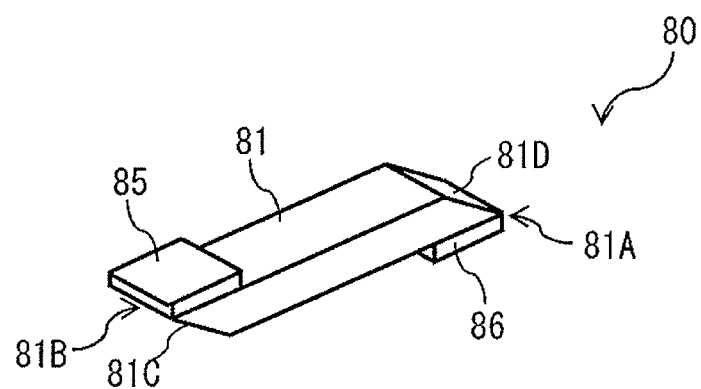

CONTACT LENS AND DETECTION METHOD

TECHNICAL FIELD

The present disclosure relates to a contact lens and a detection method.

BACKGROUND ART

Typically, as methods of acquiring biological information, there are an invasive type and a non-invasive type. Examples of the invasive type include a method of collecting blood and analyzing the blood by electrochemical reaction. On the other hand, examples of the non-invasive type include a method of emitting light from above skin and analyzing blood on the basis of an absorption spectrum of blood within blood vessels, and a method of collecting tears or sweat and analyzing the collected tears or sweat using various means.

CITATION LIST

Patent Literature

PTL 1: United States Unexamined Patent Application Publication No. 2012/0245444
PTL 2: Japanese Unexamined Patent Application Publication No. S62-133937

SUMMARY OF THE INVENTION

The invasive type has such an issue that a burden placed on a body is large. On the other hand, among the methods of the non-invasive type, the method of emitting light from above skin has such an issue that light absorption inside the skin is large, and measurement is not easy, and further, it is not easy to separate body-movement noise and a signal of a detection target. Among the methods of the non-invasive type, the method of analyzing tears or sweat described in the above-mentioned PTL has such an issue that long-term stability and heat resistance are not favorable because an electrode includes a biological material. The above-mentioned PTL also proposes configuring an electrode using an artificial composition, but in a case where an electrode includes such a material, there is such an issue that the electrode exhibits a weak response to a substance other than a detection target as well, or the electrode is easily affected by a coexistence substance or pH in a solution. It is therefore desirable to provide a contact lens and a detection method that make it possible to perform analysis with high accuracy while keeping a burden on a body small.

A contact lens according to an embodiment of the present disclosure includes a lens section attachable to an eyeball, and one or a plurality of structure portions provided in the lens section and intended to accumulate tears.

In the contact lens according to the embodiment of the present disclosure, the one or plurality of structure portions intended to accumulate tears is provided in the lens section. This makes it possible to, for example, measure an absorption spectrum of the tears, by emitting light toward the tears accumulated in the one or plurality of structure portions. Here, because the light does not pass through a large-absorption region such as skin when the light is emitted toward the tears, it is possible to, for example, measure the absorption spectrum of the tears easily. Further, it is easy to separate noise and a signal of a detection target. Furthermore, because an electrode is unnecessary, issues such as long-term stability and heat resistance attributable to an electrode, and responsiveness to a substance other than a detection target, are not present. Moreover, because this is of the non-invasive type, a burden on a body is small.

A detection method according to an embodiment of the present disclosure includes the following two.
(1) Emitting light toward tears accumulated in one or a plurality of structure portions in a contact lens that includes a lens section attachable to an eyeball, and the one or plurality of structure portions provided in the lens section and intended to accumulate tears
(2) Detecting, through the tears accumulated in the one or plurality of structure portions, transmitted light transmitted by the contact lens, reflected light reflected by the contact lens, diffracted-transmitted light diffracted and transmitted by the contact lens, or diffracted-reflected light diffracted and reflected by the contact lens, of the light emitted toward the tears accumulated in the one or plurality of structure portions In the detection method according to the embodiment of the present disclosure, the transmitted light transmitted by the contact lens, the reflected light reflected by the contact lens, the diffracted-transmitted light diffracted and transmitted by the contact lens, or the diffracted-reflected light diffracted and reflected by the contact lens, of the light emitted toward the tears accumulated in the one or plurality of structure portions provided in the lens section, is detected through the tears accumulated in the one or plurality of structure portions. This makes it possible to, for example, measure an absorption spectrum of the tears. Here, because the light does not pass through a large-absorption region such as skin when the light is emitted toward the tears, it is possible to, for example, measure the absorption spectrum of the tears easily. Further, it is easy to separate noise and a signal of a detection target. Furthermore, because an electrode is unnecessary, issues such as long-term stability and heat resistance attributable to an electrode, and responsiveness to a substance other than a detection target, are not present. Moreover, because this is of the non-invasive type, a burden on a body is small.

According to the contact lens in the embodiment of the present disclosure, the one or plurality of structure portions intended to accumulate tears is provided in the lens section, and therefore a burden on a body is small, and it is possible to perform analysis with high accuracy.

According to the detection method in the embodiment of the present disclosure, the transmitted light transmitted by the contact lens, the reflected light reflected by the contact lens, the diffracted-transmitted light diffracted and transmitted by the contact lens, or the diffracted-reflected light diffracted and reflected by the contact lens, of the light emitted toward the tears accumulated in the one or plurality of structure portions provided in the lens section, is detected through the tears accumulated in the one or plurality of structure portions, and therefore a burden on a body is small, and it is possible to perform analysis with high accuracy.

It is to be noted that effects of the present disclosure are not limited to those described above, and may be any of effects described in the present specification.

BRIEF DESCRIPTION OF DRAWINGS

FIG. 1 is a diagram illustrating an example of a state where a contact lens according to a first embodiment of the present disclosure is attached to an eyeball.

FIG. 2 is a diagram illustrating an example of a cross-sectional configuration of the contact lens and the eyeball in FIG. 1.

FIG. 3A is a diagram illustrating an example of a plane configuration of the contact lens in FIG. 1.

FIG. 3B is a diagram illustrating an example of a plane configuration of the contact lens in FIG. 1.

FIG. 3C is a diagram illustrating an example of a plane configuration of the contact lens in FIG. 1.

FIG. 3D is a diagram illustrating an example of a plane configuration of the contact lens in FIG. 1.

FIG. 3E is a diagram illustrating an example of a plane configuration of the contact lens in FIG. 1.

FIG. 3F is a diagram illustrating an example of a plane configuration of the contact lens in FIG. 1.

FIG. 3G is a diagram illustrating an example of a plane configuration of the contact lens in FIG. 1.

FIG. 4 is a diagram illustrating an example of a cross-sectional configuration of a lens section in FIG. 2.

FIG. 5 is a diagram illustrating an example of a schematic configuration of a measurement device intended to measure a component of tears accumulated in the contact lens in FIG. 1.

FIG. 6 is a diagram illustrating an example of a measurement procedure in the measurement device in FIG. 5.

FIG. 7 is a diagram illustrating an example of an absorption spectrum of each of water, glucose, protein, and lipid.

FIG. 8 is a diagram illustrating a modification example of the contact lens in FIG. 2.

FIG. 9 is a diagram illustrating a modification example of the contact lens in FIG. 2.

FIG. 10 is a diagram illustrating a modification example of the contact lens in FIG. 2.

FIG. 11 is a diagram illustrating a modification example of the contact lens in FIG. 2.

FIG. 12 is a diagram illustrating an example of a schematic configuration of a measurement device intended to measure a component of tears accumulated in the contact lens in each of FIG. 8 and FIG. 10.

FIG. 13 is a diagram illustrating an example of a schematic configuration of a measurement device intended to measure a component of tears accumulated in the contact lens in each of FIG. 9 and FIG. 11.

FIG. 14 is a diagram illustrating a modification example of the contact lens in FIG. 2.

FIG. 15 is a diagram illustrating a modification example of the contact lens in FIG. 2.

FIG. 16 is a diagram illustrating a modification example of the contact lens in FIG. 2.

FIG. 17 is a diagram illustrating a modification example of the contact lens in FIG. 2.

FIG. 18 is a diagram illustrating an example of a schematic configuration of a measurement device intended to measure a component of tears accumulated in the contact lens in each of FIG. 14 and FIG. 16.

FIG. 19 is a diagram illustrating an example of a schematic configuration of a measurement device intended to measure a component of tears accumulated in the contact lens in each of FIG. 15 and FIG. 17.

FIG. 20 is a diagram illustrating a modification example of the contact lens in FIG. 2.

FIG. 21 is a diagram illustrating a modification example of the contact lens in FIG. 2.

FIG. 22 is a diagram illustrating an example of a schematic configuration of a measurement device intended to measure a component of tears accumulated in the contact lens in each of FIG. 20 and FIG. 21.

FIG. 23 is a diagram illustrating a modification example of the contact lens in FIG. 2.

FIG. 24 is a diagram illustrating a modification example of the contact lens in FIG. 2.

FIG. 25 is a diagram illustrating an example of a schematic configuration of a measurement device intended to measure a component of tears accumulated in the contact lens in each of FIG. 23 and FIG. 24.

FIG. 26 is a diagram illustrating an example of a measurement procedure in the measurement device in FIG. 25.

FIG. 27 is a diagram illustrating an application example of a measurement device intended to measure a component of tears accumulated in the contact lens in each of FIG. 23 and FIG. 24.

FIG. 28 is a diagram illustrating an application example of a measurement device intended to measure a component of tears accumulated in the contact lens in each of FIG. 23 and FIG. 24.

FIG. 29 is a diagram illustrating an example of a path of light in a state where tears with a low concentration of a detection target substance are accumulated in a channel provided in the contact lens in each of FIG. 2, FIG. 3A, FIG. 3B, FIG. 3C, FIG. 3D, FIG. 3E, FIG. 3F, FIG. 3G, and FIG. 4.

FIG. 30 is a diagram illustrating an example of a path of light in a state where tears with a high concentration of a detection target substance are accumulated in the channel provided in the contact lens in each of FIG. 2, FIG. 3A, FIG. 3B, FIG. 3C, FIG. 3D, FIG. 3E, FIG. 3F, FIG. 3G, and FIG. 4.

FIG. 31 is a diagram illustrating an example of a path of light in a state where tears with a low concentration of a detection target substance are accumulated in a channel provided in the contact lens in each of FIG. 8 and FIG. 9.

FIG. 32 is a diagram illustrating an example of a path of light in a state where tears with a high concentration of a detection target substance are accumulated in the channel provided in the contact lens in each of FIG. 8 and FIG. 9.

FIG. 33 is a diagram illustrating an example of a path of light in a state where tears with a low concentration of a detection target substance are accumulated in a channel provided in the contact lens in each of FIG. 10 and FIG. 11.

FIG. 34 is a diagram illustrating an example of a path of light in a state where tears with a high concentration of a detection target substance are accumulated in the channel provided in the contact lens in each of FIG. 10 and FIG. 11.

FIG. 35 is a diagram illustrating an example of a path of light in a state where accumulated tears with a low concentration of a detection target substance do not fill a channel provided in the contact lens in each of FIG. 14 and FIG. 15.

FIG. 36 is a diagram illustrating an example of a path of light in a state where tears with a high concentration of a detection target substance are accumulated in the channel provided in the contact lens in each of FIG. 14 and FIG. 15.

FIG. 37 is a diagram illustrating an example of a path of light in a state where tears with a low concentration of a detection target substance are accumulated in a channel provided in the contact lens in each of FIG. 16 and FIG. 17.

FIG. 38 is a diagram illustrating an example of a path of light in a state where tears with a high concentration of a detection target substance are accumulated in the channel provided in the contact lens in each of FIG. 16 and FIG. 17.

FIG. 39 is a diagram illustrating an example of a path of light in a state where tears with a low concentration of a detection target substance are accumulated in a channel provided in the contact lens in each of FIG. 20 and FIG. 23.

FIG. 40 is a diagram illustrating an example of a path of light in a state where tears with a high concentration of a detection target substance are accumulated in the channel provided in the contact lens in each of FIG. 20 and FIG. 23.

FIG. 41 is a diagram illustrating an example of a path of light in a state where tears with a low concentration of a detection target substance are accumulated in a channel provided in the contact lens in each of FIG. 21 and FIG. 24.

FIG. 42 is a diagram illustrating an example of a path of light in a state where tears with a high concentration of a detection target substance are accumulated in the channel provided in the contact lens in each of FIG. 21 and FIG. 24.

FIG. 43 is a horizontal cross-sectional view of a modification example of a structure portion provided in the contact lens in each of FIG. 2, FIG. 3A, FIG. 3B, FIG. 3C, FIG. 3D, FIG. 3E, FIG. 3F, FIG. 3G, FIG. 8 to FIG. 11, FIG. 14 to FIG. 17, FIG. 20, FIG. 21, FIG. 23, FIG. 24, and FIG. 29 to FIG. 42.

FIG. 44 is a vertical cross-sectional view of a modification example of the structure portion in FIG. 43.

FIG. 45 is a horizontal cross-sectional view of a modification example of the structure portion provided in the contact lens in each of FIG. 2, FIG. 3A, FIG. 3B, FIG. 3C, FIG. 3D, FIG. 3E, FIG. 3F, FIG. 3G, FIG. 8 to FIG. 11, FIG. 14 to FIG. 17, FIG. 20, FIG. 21, FIG. 23, FIG. 24, and FIG. 29 to FIG. 42.

FIG. 46 is a diagram illustrating a modification example of glasses in FIG. 28.

FIG. 47 is a diagram illustrating an example of a state where a contact lens according to a second embodiment of the present disclosure is attached to an eyeball.

FIG. 48 is a diagram illustrating an example of a cross-sectional configuration of the contact lens and the eyeball in FIG. 47.

FIG. 49 is a diagram illustrating an example of a structure provided in the contact lens in FIG. 48.

FIG. 50 is a diagram illustrating an example of a structure provided in the contact lens in FIG. 48.

FIG. 51 is a diagram illustrating an example of a structure provided in the contact lens in FIG. 48.

FIG. 52 is a diagram illustrating an example of a judgement procedure for a state of a living body using the contact lens in FIG. 47.

FIG. 53 is a diagram illustrating a modification example of the contact lens in FIG. 47.

FIG. 54 (A) is a diagram illustrating a modification example of a plane configuration of a color index and a structure in FIG. 53. (B) is a diagram illustrating a modification example of a cross-sectional configuration at a line A-A of the color index and the structure in FIG. 53.

FIG. 55 is a diagram illustrating a modification example of a plane configuration of the color index and the structure in FIG. 53.

FIG. 56 (A) is a diagram illustrating a modification example of a plane configuration of the color index and the structure in FIG. 53. (B) is a diagram illustrating a modification example of a cross-sectional configuration at a line A-A of the color index and the structure in FIG. 53.

FIG. 57 is a diagram illustrating a modification example of the color index and the structure in FIG. 53.

FIG. 58 is a diagram illustrating a modification example of a structure provided in the contact lens in FIG. 48.

MODES FOR CARRYING OUT THE INVENTION

Some embodiments of the present disclosure are described below in detail with reference to the drawings. It is to be noted that the description is given in the following order.

1. First Embodiment

An example in which a channel that accumulates tears is provided in a lens section (FIG. 1 to FIG. 6)

2. Modification Examples of First Embodiment

Modification Example A

An example in which a reflection layer is provided in the lens section (FIG. 8 to FIG. 11)

Modification Example B

An example in which a diffraction element is provided in the lens section (FIG. 14 to FIG. 17)

Modification Example C

An example in which the reflection layer and the diffraction element are provided in the lens section (FIG. 20, FIG. 21, FIG. 23, and FIG. 24)

Modification Example D

An example in which the channel of the lens section has a prism shape (FIG. 29 to FIG. 44)

Modification Example E

An example in which a suction chamber is coupled to the channel of the lens section (FIG. 43 and FIG. 44)

Modification Example F

An example in which a suction chamber and a storage chamber are coupled to the channel of the lens section (FIG. 45)

Modification Example G

An example in which a measurement device and a medicinal-solution supply device are provided in glasses (FIG. 46)

3. Second Embodiment

An example in which a channel that accumulates tears and doubles as a light-guiding path is provided in a lens section (FIG. 47 to FIG. 52)

4. Modification Examples of Second Embodiment

An example in which an index is provided (FIG. 53 to FIG. 57)

An example in which a sealing layer is provided (FIG. 58)

1. First Embodiment

[Configuration]

A contact lens 1 according to a first embodiment of the present disclosure is described. FIG. 1 illustrates an example of a state where the contact lens 1 is attached to an eyeball 100. FIG. 2 illustrates an example of a cross-sectional configuration of the contact lens 1 and the eyeball 100. The contact lens 1 includes a lens section 10 attachable to the eyeball 100, and one or a plurality of structure portions 20 provided in the lens section 10. The one or plurality of structure portions 20 is a structure intended to accumulate tears.

The lens section 10 has a curved-plane shape that resembles a surface shape of the eyeball 100. The lens section 10 is, for example, circular when viewed from front. The lens section 10 has a diameter having a value larger than that of a diameter of an outer edge of an iris 110. The lens section 10 may be a lens having an eyesight correction function intended to correct nearsightedness, farsightedness, astigmatism, etc., or may be a lens not having such an eyesight correction function.

The one or plurality of structure portions 20 is formed, for example, to avoid a middle of the lens section 10. The one or plurality of structure portions 20 is formed, for example, as illustrated in FIG. 3A to FIG. 3G, to avoid a point opposed to a pupil 120, when the contact lens 1 is attached to the eyeball 100. The one or plurality of structure portions 20 includes, for example, a channel 21 provided inside the lens section 10. The channel 21 has, for example, a spiral shape around the middle of the lens section 10, as illustrated in FIG. 3A to FIG. 3D. The channel 21 may be formed, for example, in a circular pattern as illustrated in FIG. 3A to FIG. 3C, or may be formed, for example, in a quadrangle pattern as illustrated in FIG. 3D. The lens section 10 may be, for example, provided with the one structure portion 20 (i.e., the one channel 21) as illustrated in FIG. 3A to FIG. 3D, or may be, for example, provided with the two structure portions 20 (i.e., the two channels 21) as illustrated in FIG. 3E to FIG. 3G.

It is to be noted that, in a case where the lens section 10 is provided with the two structure portions 20 (i.e., the two channels 21), the two structure portions 20 (i.e., the two channels 21) may be disposed at respective positions opposed to each other with the middle of the lens section 10 interposed therebetween. Further, in this case, the channel 21 may have, for example, a zigzag shape as illustrated in FIG. 3E to FIG. 3G. Furthermore, in this case, for example, as illustrated in FIG. 3F and FIG. 3G, a pair of an inlet 21A and an outlet 21B provided in the one structure portion 20 (i.e., the one channel 21) and a pair of the inlet 21A and the outlet 21B provided in the other structure portion 20 (i.e., the other channel 21) may be disposed at respective positions that have left-right symmetry with respect to the middle of the lens section 10. At this time, further, each of the inlets 21A may be disposed at a position close to an edge of the lens section 10, in the channel 21 provided with the inlet 21A. Furthermore, as for the inlet 21A and the outlet 21B, in the structure portion 20 relatively close to a lacrimal gland when the contact lens 1 is attached to the eyeball 100, the inlet 21A may be configured to be disposed at a position relatively close to the lacrimal gland as compared with the outlet 21B. It is to be noted that, in FIG. 3F, each of the inlets 21A and each of the outlets 21B are each disposed at a position close to the edge of the lens section 10, in both of the structure portions 20. Further, in FIG. 3G, each of the inlets 21A is disposed at a position close to the edge of the lens section 10, and each of the outlets 21B is disposed at a position close to the middle of the lens section 10, in both of the structure portions 20.

Incidentally, the channel 21 includes, for example, the inlet 21A for tears and the outlet 21B for tears, as illustrated in FIG. 3A to FIG. 3G and FIG. 4. The inlet 21A and the outlet 21B are exposed, for example, on a surface on side to be in contact with the eyeball 100, of the lens section 10. It is to be noted that at least one of the inlet 21A or the outlet 21B may be exposed on a surface on side not to be in contact with the eyeball 100, of the lens section 10. The inlet 21A is, for example, disposed at a position close to the edge of the lens section 10, in the channel 21. In other words, the inlet 21A is, for example, disposed at a position relatively close to the lacrimal gland as compared with the outlet 21B, when the contact lens 1 is attached to the eyeball 100. The channel 21 includes an inflow path 21$f$ coupled to the inlet 21A, and a discharge path 21$e$ coupled to the inflow path 21$f$ and the outlet 21B. It is preferable that the inflow path 21$f$ have, for example, a width that makes it possible to draw tears in by a capillary phenomenon, and it is preferable that the discharge path 21$e$ have, for example, a width wider than that of the inflow path 21$f$. The width of the discharge path 21$e$ is, for example, a distance that does not cause (or makes it difficult to cause) the capillary phenomenon. The channel 21 is provided, for example, inside the lens section 10, as illustrated in FIG. 4.

FIG. 5 illustrates an example of a schematic configuration of a measurement device 2 intended to measure a component of tears accumulated in the contact lens 1. The measurement device 2 corresponds to a specific example of a "detection device" of the present disclosure. The measurement device 2 includes, for example, a support section 30 that supports the contact lens 1 having tears accumulated in the one or plurality of structure portions 20, and a light source section 40 that emits light toward the tears accumulated in the one or plurality of structure portions 20 in the contact lens 1. The measurement device 2 further includes, for example, a light receiving section 50 that receives light (transmitted light Lb) transmitted by the contact lens 1, through the tears accumulated in the one or plurality of structure portions 20, of the light (irradiation light La) emitted from the light source section 40. The measurement device 2 further includes, for example, a signal processing section 60 that determines a state of a living body by analyzing a detection signal outputted from the light receiving section 50, and a display section 70 that displays a result determined by the signal processing section 60. The display section 70 may be omitted. In this case, the measurement device 2 includes, for example, a communication section that outputs the result determined by the signal processing section 60 to an external apparatus with a display section.

The light source section 40 includes, for example, a light source with a single wavelength or a plurality of wavelengths. Examples of the light source included in the light source section 40 include a laser with a single wavelength, a laser with a plurality of wavelengths, an LED with a single wavelength, an LED with a plurality of wavelengths, an LED with white light, UV light, visible light, or infrared light, etc. The light receiving section 50 includes, for example, a photodiode, etc. The signal processing section 60 includes, for example, an integrated circuit IC that executes a measurement procedure described later, etc. The display section 70 displays, for example, an image on the basis of an image signal from the signal processing section 60.

Next, an example of the measurement procedure in the measurement device 2 is described. FIG. 6 illustrates an example of the measurement procedure in the measurement device 2. First, a user attaches the contact lens 1 to the eyeball 100 of the user. Then, tears are accumulated in the one or plurality of structure portions 20 (the channel 21) provided in the contact lens 1, by utilizing, for example, the capillary phenomenon. Next, the user removes the contact lens 1 having the tears accumulated in the one or plurality of structure portions 20 from the eyeball 100, and attaches the removed contact lens 1 to the measurement device 2 (step S101). Specifically, the user allows the support section 30 to support the contact lens 1 having the tears accumulated in the one or plurality of structure portions 20. As a result, for example, the contact lens 1 is fixed to the support section 30.

Next, the user activates the measurement device 2. Then, the light source section 40 emits the light (the irradiation light La) toward the tears accumulated in the one or plurality of structure portions 20 (the channel 21) in the contact lens 1, and the light receiving section 50 detects the light (the transmitted light Lb) through the contact lens 1 (step S102). Specifically, the light receiving section 50 detects the light (the transmitted light Lb) transmitted by the contact lens 1, through the tears accumulated in the one or plurality of structure portions 20, of the light (the irradiation light La) emitted toward the tears accumulated in the one or plurality of structure portions 20. The light receiving section 50 outputs the detection signal generated by receiving the transmitted light Lb to the signal processing section 60.

Next, the signal processing section 60 analyzes the inputted detection signal, and determines the state of the living body (step S103). Specifically, the signal processing section 60 derives an absorption spectrum of the tears on the basis of the inputted detection signal, and estimates, for example, a type and a concentration of a component included in the tears, from the derived absorption spectrum. The signal processing section 60 determines the state of the living body, on the basis of the estimated type and concentration of the component of the tears. The signal processing section 60 outputs a determination result to the display section 70 as an image signal. The display section 70 displays an image (the determination result) on the basis of the image signal inputted from the signal processing section 60. It is to be noted that the determination of the state of the living body may be performed by an external apparatus. In this case, the signal processing section 60 may analyze the inputted detection signal, and output an analysis result to the external apparatus through a communication section.

FIG. 7 illustrates an example of an absorption spectrum of each of water, glucose, protein, and lipid. FIG. 7 illustrates an example of an absorption spectrum when water, glucose, protein, or lipid is included in a sample at a predetermined concentration. The signal processing section 60 compares the obtained absorption spectrum and, for example, the absorption spectrum of glucose, protein, or lipid illustrated in FIG. 7, and determines an analogy therebetween. As a result, for example, in a case where the obtained absorption spectrum is similar to the absorption spectrum of glucose, the signal processing section 60 determines that glucose is included in the tears. Further, the signal processing section 60 estimates the concentration of glucose included in the tears, by comparing a peak value of the obtained absorption spectrum and a peak value of glucose illustrated in FIG. 7. In this way, the measurement device 2 determines the state of the living body from the tears.

[Effects]

Next, effects of the contact lens 1 and the measurement device 2 of the present embodiment are described.

Typically, as methods of acquiring biological information, there are an invasive type and a non-invasive type. Examples of the invasive type include a method of collecting blood and analyzing the blood by electrochemical reaction. On the other hand, examples of the non-invasive type include a method of emitting light from above skin and analyzing blood on the basis of an absorption spectrum of blood within blood vessels, and a method of collecting tears or sweat and analyzing the collected tears or sweat using various means.

The invasive type has such an issue that a burden placed on a body is large. On the other hand, among the methods of the non-invasive type, the method of emitting light from above skin has such an issue that light absorption inside the skin is large, and measurement is not easy, and further, it is not easy to separate body-movement noise and a signal of a detection target. Among the methods of the non-invasive type, the method of analyzing tears or sweat described in the above-mentioned PTL has such an issue that long-term stability and heat resistance are not favorable because an electrode includes a biological material. The above-mentioned PTL also proposes configuring an electrode using an artificial composition, but in a case where an electrode includes such a material, there is such an issue that the electrode exhibits a weak response to a substance other than a detection target as well, or the electrode is easily affected by a coexistence substance or pH in a solution.

In contrast, in the contact lens 1 of the present embodiment, the lens section 10 is provided with the one or plurality of structure portions 20 intended to accumulate tears. This makes it possible to, for example, measure the absorption spectrum of the tears, by emitting the light toward the tears accumulated in the one or plurality of structure portions 20. Here, because the light does not pass through a large-absorption region such as skin when the light is emitted toward the tears, it is possible to, for example, measure the absorption spectrum of the tears easily. Further, it is easy to separate noise and a signal of a detection target. Furthermore, because an electrode is unnecessary, issues such as long-term stability and heat resistance attributable to an electrode, and responsiveness to a substance other than a detection target, are not present. Moreover, because this is of the non-invasive type, a burden on a body is small. This makes it possible to perform analysis with high accuracy while keeping a burden on a body small.

Further, in the present embodiment, the one or plurality of structure portions 20 is formed to avoid the middle of the lens section 10. This makes it possible to prevent a view from being blocked by the one or plurality of structure portions 20, thereby making it possible to collect the tears of the user while the user uses the contact lens 1 in everyday life.

Furthermore, in the present embodiment, the one or plurality of structure portions 20 includes the channel 21 provided inside the lens section 10. This makes it possible to prevent formation of projections and depressions on the surface of the lens section 10 due to presence of the channel 21, thereby making it possible to avoid deterioration of usability of the contact lens 1 for the user due to the presence of the channel 21.

Further, in the present embodiment, the channel 21 includes the inflow path 21f that makes it possible to draw the tears in by the capillary phenomenon, and further includes the discharge path 21e having the width wider than that of the inflow path 21f. This makes it possible to collect the tears efficiently.

Furthermore, in the present embodiment, in a case where an entrance of the inflow path 21f is disposed at a position close to the edge of the lens section 10 in the channel 21, it is possible to collect the tears efficiently, in a process where the tears flow from the lacrimal gland to a lacrimal point. Further, in the present embodiment, in a case where: the two structure portions 20 (i.e., the two channels 21) are disposed at the respective positions opposed to each other with the middle of the lens section 10 interposed therebetween; the pair of the inlet 21A and the outlet 21B provided in the one structure portion 20 (i.e., the one channel 21) and the pair of the inlet 21A and the outlet 21B provided in the other structure portion 20 (i.e., the other channel 21) are disposed at the respective positions that have left-right symmetry with respect to the middle of the lens section 10; each of the inlets 21A is disposed at the position close to the edge of the lens section 10, in the channel 21 provided with the inlet 21A; and the inlet 21A in the structure portion 20 relatively close to the lacrimal gland is disposed at the position relatively close to the lacrimal gland as compared with the outlet 21B, when the contact lens 1 is attached to the eyeball 100, it is possible to collect the tears efficiently in the process where the tears flow from the lacrimal gland to the lacrimal point, on whichever side, left side or right side, the contact lens 1 is used for the eyeball 100.

Moreover, in the present embodiment, of the light (the irradiation light La) emitted toward the tears accumulated in the one or plurality of structure portions 20, the light (the transmitted light Lb) transmitted by the contact lens 1 is detected by the light receiving section 50, through the tears accumulated in the one or plurality of structure portions 20. This makes it possible to, for example, measure the absorption spectrum of the tears, by emitting the light toward the tears accumulated in the one or plurality of structure portions 20. Here, because the light does not pass through a large-absorption region such as skin when the light is emitted toward the tears, it is possible to, for example, measure the absorption spectrum of the tears easily. Further, it is easy to separate noise and a signal of a detection target. Furthermore, because an electrode is unnecessary, issues such as long-term stability and heat resistance attributable to an electrode, and responsiveness to a substance other than a detection target, are not present. Moreover, because this is of the non-invasive type, a burden on a body is small. This makes it possible to perform analysis with high accuracy while keeping a burden on a body small.

2. Modification Examples of First Embodiment

Next, modification examples of the contact lens 1 and the measurement device 2 according to the first embodiment are described.

Modification Example A

FIG. 8 and FIG. 9 illustrate a modification example of the contact lens 1 in FIG. 2. In the present modification example, the contact lens 1 further includes a reflection layer 22 disposed to be opposed to the channel 21 in a thickness direction of the lens section 10. The reflection layer 22 is configured to enable reflection of the light from the light source section 40, and includes, for example, a dielectric multilayer film, a metallic film, a hologram, etc. The reflection layer 22 is disposed, for example, on the surface (a convex-shaped surface 10A) on the side not to be in contact with the eyeball 100, of the lens section 10, or the surface (a concave-shaped surface 10B) on the side to be in contact with the eyeball 100, of the lens section 10. It is to be noted that, for example, as illustrated in FIG. 10 and FIG. 11, the reflection layer 22 may be formed inside the lens section 10. At this time, the reflection layer 22 may be provided in contact with the surface of the channel 21, or may be provided to be a portion of an inner surface of the channel 21.

FIG. 12 illustrates an example of a schematic configuration of the measurement device 2 intended to measure the component of the tears accumulated in the contact lens 1 in each of FIG. 8 and FIG. 10. It is to be noted that the contact lens 1 in FIG. 8 is exemplified in FIG. 12. FIG. 13 illustrates an example of a schematic configuration of the measurement device 2 intended to measure the component of the tears accumulated in the contact lens 1 in each of FIG. 9 and FIG. 11. It is to be noted that the contact lens 1 in FIG. 9 is exemplified in FIG. 13. The measurement device 2 includes, for example, the support section 30 that supports the contact lens 1 having the tears accumulated in the one or plurality of structure portions 20, and the light source section 40 that emits the light toward the tears accumulated in the one or plurality of structure portions 20 in the contact lens 1. The measurement device 2 further includes, for example, the light receiving section 50 that receives light (reflected light Lc) reflected by the contact lens 1, through the tears accumulated in the one or plurality of structure portions 20, of the light (the irradiation light La) emitted from the light source section 40. The measurement device 2 further includes, for example, the signal processing section 60 and the display section 70. The display section 70 may be omitted. In this case, the measurement device 2 includes, for example, a communication section that outputs a determination result or an analysis result obtained by the signal processing section 60 to an external apparatus with a display section.

Next, an example of the measurement procedure in the measurement device 2 is described. First, the user attaches the contact lens 1 to the eyeball 100 of the user. Then, the tears are accumulated in the one or plurality of structure portions 20 (the channel 21) provided in the contact lens 1, by utilizing, for example, the capillary phenomenon. Next, the user removes the contact lens 1 having the tears accumulated in the one or plurality of structure portions 20 from the eyeball 100, and attaches the removed contact lens 1 to the measurement device 2 (step S101). Specifically, the user allows the support section 30 to support the contact lens 1 having the tears accumulated in the one or plurality of structure portions 20. As a result, for example, the contact lens 1 is fixed to the support section 30.

Next, the user activates the measurement device 2. Then, the light source section 40 emits the light (the irradiation light La) toward the tears accumulated in the one or plurality of structure portions 20 (the channel 21) in the contact lens 1, and the light receiving section 50 detects the light (the reflected light Lc) through the contact lens 1 (step S102). Specifically, the light receiving section 50 detects the light (the reflected light Lc) transmitted by the tears accumulated in the one or plurality of structure portions 20, reflected by the reflection layer 22, and transmitted by the accumulated tears again, of the light (the irradiation light La) emitted toward the tears accumulated in the one or plurality of structure portions 20. The light receiving section 50 outputs the detection signal generated by receiving the reflected light Lc to the signal processing section 60. The signal processing section 60 analyzes the inputted detection signal, and determines the state of the living body using, for example, the above-described analysis method (step S103).

In the present modification example, the reflection layer 22 disposed to be opposed to the channel 21 in the thickness direction of the lens section 10 is provided. This makes it possible to dispose the light receiving section 50 on the same side as the side where the light source section 40 is disposed, in a positional relationship with the contact lens 1, thereby making it unnecessary to provide a space for the light receiving section 50 on the side opposite to the side where the light source section 40 is disposed, in the positional relationship with the contact lens 1. As a result, because it is not necessary to provide the space for the light receiving section 50 on the side opposite to the side where the light source section 40 is disposed, in the positional relationship with the contact lens 1, it is possible to downsize the measurement device 2 accordingly. Further, in a case where the reflection layer 22 is formed inside the lens section 10, the reflection layer 22 does not touch the eyeball 100, thereby making it possible to reduce the burden on the body further.

Modification Example B

FIG. 14 and FIG. 15 illustrate a modification example of the contact lens 1 in FIG. 2. In the present modification example, the contact lens 1 further includes a diffraction element 23 disposed to be opposed to the channel 21 in the thickness direction of the lens section 10. The diffraction element 23 is configured to allow refraction of the light from the light source section 40 in a predetermined direction, and includes, for example, a holo-graphic optical element (HOE: Holo-graphic Optical Element). The diffraction element 23 is disposed, for example, on the surface (the concave-shaped surface 10B) on the side to be in contact with the eyeball 100, of the lens section 10, or on the surface (the convex-shaped surface 10A) on the side not to be in contact with the eyeball 100, of the lens section 10. It is to be noted that, for example, as illustrated in FIG. 16 and FIG. 17, the diffraction element 23 may be formed inside the lens section 10. At this time, the diffraction element 23 may be provided in contact with the surface of the channel 21, or may be provided to be a portion of the inner surface of the channel 21.

FIG. 18 illustrates an example of a schematic configuration of the measurement device 2 intended to measure the component of the tears accumulated in the contact lens 1 in each of FIG. 14 and FIG. 16. It is to be noted that the contact lens 1 in FIG. 14 is exemplified in FIG. 18. FIG. 19 illustrates an example of a schematic configuration of the measurement device 2 intended to measure the component of the tears accumulated in the contact lens 1 in each of FIG. 15 and FIG. 17. It is to be noted that the contact lens 1 in FIG. 15 is exemplified in FIG. 19. The measurement device 2 includes, for example, the support section 30 that supports the contact lens 1 having the tears accumulated in the one or plurality of structure portions 20, and the light source section 40 that emits the light toward the tears accumulated in the one or plurality of structure portions 20 in the contact lens 1. The measurement device 2 further includes, for example, the light receiving section 50 that receives light (diffracted-transmitted light Ld) diffracted and transmitted by the contact lens 1, through the tears accumulated in the one or plurality of structure portions 20, of the light (the irradiation light La) emitted from the light source section 40. The measurement device 2 further includes, for example, the signal processing section 60 and the display section 70. The display section 70 may be omitted. In this case, the measurement device 2 includes, for example, a communication section that outputs a determination result or an analysis result obtained by the signal processing section 60 to an external apparatus with a display section.

Next, an example of the measurement procedure in the measurement device 2 is described. First, the user attaches the contact lens 1 to the eyeball 100 of the user. Then, the tears are accumulated in the one or plurality of structure portions 20 (the channel 21) provided in the contact lens 1, by utilizing, for example, the capillary phenomenon. Next, the user removes the contact lens 1 having the tears accumulated in the one or plurality of structure portions 20 from the eyeball 100, and attaches the removed contact lens 1 to the measurement device 2 (step S101). Specifically, the user allows the support section 30 to support the contact lens 1 having the tears accumulated in the one or plurality of structure portions 20. As a result, for example, the contact lens 1 is fixed to the support section 30.

Next, the user activates the measurement device 2. Then, the light source section 40 emits the light (the irradiation light La) toward the tears accumulated in the one or plurality of structure portions 20 (the channel 21) in the contact lens 1, and the light receiving section 50 detects the light (the diffracted-transmitted light Ld) through the contact lens 1 (step S102). Specifically, the light receiving section 50 detects the light (the diffracted-transmitted light Ld) diffracted by the diffraction element 23 and transmitted by the tears accumulated in the one or plurality of structure portions 20, of the light (the irradiation light La) emitted toward the tears accumulated in the one or plurality of structure portions 20. The light receiving section 50 outputs the detection signal generated by receiving the diffracted-transmitted light Ld to the signal processing section 60. The signal processing section 60 analyzes the inputted detection signal, and determines the state of the living body using, for example, the above-described analysis method (step S103). It is to be noted that the determination of the state of the living body may be performed by an external apparatus. In this case, the signal processing section 60 may analyze the inputted detection signal, and output an analysis result to the external apparatus through a communication section.

In the present modification example, the diffraction element 23 disposed to be opposed to the channel 21 in the thickness direction of the lens section 10 is provided. This makes it possible to separate and remove light other than desirable light by diffraction, thereby making it possible to, for example, measure the absorption spectrum of the tears with accuracy. Here, because the light does not pass through a large-absorption region such as skin when the light is emitted toward the tears, it is possible to, for example, measure the absorption spectrum of the tears easily. Further, it is easy to separate noise and a signal of a detection target. Furthermore, because an electrode is unnecessary, issues such as long-term stability and heat resistance attributable to an electrode, and responsiveness to a substance other than a detection target, are not present. Moreover, because this is of the non-invasive type, a burden on a body is small. This makes it possible to perform analysis with high accuracy while keeping a burden on a body small. Further, in a case where the diffraction element 23 is formed inside the lens section 10, the diffraction element 23 does not touch the eyeball 100, thereby making it possible to reduce the burden on the body further.

Modification Example C

FIG. 20 illustrates a modification example of the contact lens 1 in FIG. 2. In the present modification example, the contact lens 1 further includes the reflection layer 22 and the diffraction element 23. The reflection layer 22 and the diffraction element 23 are both disposed to be opposed to the channel 21 in the thickness direction of the lens section 10. The reflection layer 22 is disposed on the surface (the convex-shaped surface 10A) on the side not to be in contact with the eyeball 100, of the lens section 10. The diffraction element 23 is disposed on the surface (the concave-shaped surface 10B) on the side to be in contact with the eyeball 100, of the lens section 10. It is to be noted that, for example, as illustrated in FIG. 21, the reflection layer 22 and the diffraction element 23 may be formed inside the lens section 10. At this time, the reflection layer 22 and the diffraction element 23 may be provided in contact with the surface of the channel 21, or may be provided to be a portion of the inner surface of the channel 21.

FIG. 22 illustrates an example of a schematic configuration of the measurement device 2 intended to measure the component of the tears accumulated in the contact lens 1 in each of FIG. 20 and FIG. 21. It is to be noted that the contact lens 1 in FIG. 20 is exemplified in FIG. 22. The measurement device 2 includes, for example, the support section 30 that supports the contact lens 1 having the tears accumulated in the one or plurality of structure portions 20, and the light source section 40 that emits the light toward the tears accumulated in the one or plurality of structure portions 20 in the contact lens 1. The measurement device 2 further includes, for example, the light receiving section 50 that receives light (diffracted-reflected light Le) diffracted and reflected by the contact lens 1, through the tears accumulated in the one or plurality of structure portions 20, of the light (the irradiation light La) emitted from the light source section 40. The measurement device 2 further includes, for example, the signal processing section 60 and the display section 70. The display section 70 may be omitted. In this case, the measurement device 2 includes, for example, a communication section that outputs a determination result or an analysis result obtained by the signal processing section 60 to an external apparatus with a display section.

Next, an example of the measurement procedure in the measurement device 2 is described. First, the user attaches the contact lens 1 to the eyeball 100 of the user. Then, the tears are accumulated in the one or plurality of structure portions 20 (the channel 21) provided in the contact lens 1, by utilizing, for example, the capillary phenomenon. Next, the user removes the contact lens 1 having the tears accumulated in the one or plurality of structure portions 20 from the eyeball 100, and attaches the removed contact lens 1 to the measurement device 2 (step S101). Specifically, the user allows the support section 30 to support the contact lens 1 having the tears accumulated in the one or plurality of structure portions 20. As a result, for example, the contact lens 1 is fixed to the support section 30.

Next, the user activates the measurement device 2. Then, the light source section 40 emits the light (the irradiation light La) toward the tears accumulated in the one or plurality of structure portions 20 (the channel 21) in the contact lens 1, and the light receiving section 50 detects the light (the diffracted-reflected light Le) through the contact lens 1 (step S102). Specifically, the light receiving section 50 detects the light (the diffracted-reflected light Le) diffracted by the diffraction element 23, transmitted by the tears accumulated in the one or plurality of structure portions 20, reflected by the reflection layer 22, and transmitted by the accumulated tears and diffracted by the diffraction element 23 again, of the light (the irradiation light La) emitted toward the tears accumulated in the one or plurality of structure portions 20.

The light receiving section 50 outputs the detection signal generated by receiving the diffracted-reflected light Le to the signal processing section 60. The signal processing section 60 analyzes the inputted detection signal, and determines the state of the living body using, for example, the above-described analysis method (step S103).

In the present modification example, the reflection layer 22 and the diffraction element 23 are provided. This makes it possible to dispose the light receiving section 50 on the same side as the side where the light source section 40 is disposed, in the positional relationship with the contact lens 1, thereby making it unnecessary to provide a space for the light receiving section 50 on the side opposite to the side where the light source section 40 is disposed, in the positional relationship with the contact lens 1. As a result, because it is not necessary to provide the space for the light receiving section 50 on the side opposite to the side where the light source section 40 is disposed, in the positional relationship with the contact lens 1, it is possible to downsize the measurement device 2 accordingly. Further, in a case where the reflection layer 22 and the diffraction element 23 are formed inside the lens section 10, the reflection layer 22 and the diffraction element 23 do not touch the eyeball 100, thereby making it possible to reduce the burden on the body further.

Modification Example D

FIG. 23 illustrates a modification example of the contact lens 1 in FIG. 2. In the present modification example, the contact lens 1 further includes the reflection layer 22 and the diffraction element 23. The reflection layer 22 and the diffraction element 23 are both disposed to be opposed to the channel 21 in the thickness direction of the lens section 10. In the present modification example, the reflection layer 22 is disposed on the surface (the concave-shaped surface 10B) on the side to be in contact with the eyeball 100, of the lens section 10. The reflection layer 22 is disposed at a position closer to the eyeball 100 than the channel 21 is when the contact lens 1 is attached to the eyeball 100. The diffraction element 23 is disposed on the surface (the convex-shaped surface 10A) on the side not to be in contact with the eyeball 100, of the lens section 10. The diffraction element 23 is disposed at a position farther from the eyeball 100 than the channel 21 is when the contact lens 1 is attached to the eyeball 100. It is to be noted that, for example, as illustrated in FIG. 24, the reflection layer 22 and the diffraction element 23 may be formed inside the lens section 10. At this time, the reflection layer 22 and the diffraction element 23 may be provided in contact with the surface of the channel 21, or may be provided to be a portion of the inner surface of the channel 21.

FIG. 25 illustrates an example of a schematic configuration of the measurement device 2 intended to measure the component of the tears accumulated in the contact lens 1 in each of FIG. 23 and FIG. 24. It is to be noted that the contact lens 1 in FIG. 23 is exemplified in FIG. 25. In the present modification example, the measurement device 2 measures the component of the tears accumulated in the contact lens 1 remaining attached to the eyeball 100. The measurement device 2 includes, for example, the light source section 40 that emits the light toward the tears accumulated in the one or plurality of structure portions 20 in the contact lens 1. At this time, the user sets an optical axis of the irradiation light La to prevent most of the irradiation light La from entering a retina within the eyeball 100 even if the light (the irradiation light La) emitted from the light source section 40 enters the eyeball 100 without intervention of the diffraction element 23. In other words, it is preferable to allow the irradiation light La to enter the diffraction element 23 at a considerably shallow angle.

The measurement device 2 further includes, for example, the light receiving section 50 that receives the light (the diffracted-reflected light Le) diffracted and reflected by the contact lens 1, through the tears accumulated in the one or plurality of structure portions 20, of the irradiation light La. The measurement device 2 further includes, for example, the signal processing section 60 and the display section 70. The display section 70 may be omitted. In this case, the measurement device 2 includes, for example, a communication section that outputs a determination result or an analysis result obtained by the signal processing section 60 to an external apparatus with a display section.

Next, an example of a measurement procedure in the measurement device 2 is described. FIG. 26 illustrates an example of the measurement procedure in the measurement device 2. First, the user attaches the contact lens 1 to the eyeball 100 of the user (step S201). Then, the tears are accumulated in the one or plurality of structure portions 20 (the channel 21) provided in the contact lens 1, by utilizing, for example, the capillary phenomenon. Next, the user installs the measurement device 2 at a predetermined position, while the contact lens 1 having the tears accumulated in the one or plurality of structure portions 20 remains attached to the eyeball 100. Specifically, the user adjusts a position and an orientation of the measurement device 2 with respect to the contact lens 1 to allow the irradiation light La to enter the diffraction element 23 at a considerably shallow angle.

Next, the user activates the measurement device 2. Then, the light source section 40 emits the light (the irradiation light La) toward the tears accumulated in the one or plurality of structure portions 20 (the channel 21) in the contact lens 1 in a state of being attached to the eyeball 100, and the light receiving section 50 detects the light (the diffracted-reflected light Le) through the contact lens 1 (step S202). Specifically, the light receiving section 50 detects the light (the diffracted-reflected light Le) diffracted by the diffraction element 23, transmitted by the tears accumulated in the one or plurality of structure portions 20, reflected by the reflection layer 22, and transmitted by the accumulated tears and diffracted by the diffraction element 23 again, of the light (the irradiation light La) emitted toward the tears accumulated in the one or plurality of structure portions 20. The light receiving section 50 outputs the detection signal generated by receiving the diffracted-reflected light Le to the signal processing section 60. The signal processing section 60 analyzes the inputted detection signal, and determines the state of the living body using, for example, the above-described analysis method (step S203).

In the present modification example, the reflection layer 22 and the diffraction element 23 are provided. This makes it possible to dispose the light receiving section 50 on the same side as the side where the light source section 40 is disposed, in the positional relationship with the contact lens 1, thereby making it unnecessary to provide a space for the light receiving section 50 on the support section 30. As a result, because it is not necessary to provide the space for the light receiving section 50 on the support section 30, it is possible to downsize the measurement device 2 accordingly. Further, in the present modification example, the diffraction element 23 is disposed on the surface (the convex-shaped surface) on the side not to be in contact with the eyeball 100, of the lens section 10. This makes it possible to measure the absorption spectrum of the tears while the contact lens 1 remains attached to the eyeball 100. Moreover, in a case where the reflection layer 22 and the diffraction element 23 are formed inside the lens section 10, the reflection layer 22 and the diffraction element 23 do not touch the eyeball 100, thereby making it possible to reduce the burden on the body further.

In the present modification example, the measurement device 2 may be, for example, built in a mobile terminal 3, as illustrated in FIG. 27. This makes it possible to carry the measurement device 2 easily. Further, in the present modification example, the measurement device 2 may be built in, for example, glasses 4, as illustrated in FIG. 28. At this time, the glasses 4 include a lens frame 41, and a temple 42 rotatably fixed to an end portion of the lens frame 41. The measurement device 2 in the present modification example is provided, for example, in the temple 42. In this way, in the case where the measurement device 2 is built in the glasses 4, the user is enabled to adjust the position and the orientation of the measurement device 2, only by wearing the glasses 4. It is to be noted that the glasses 4 may be provided with or may not be provided with lenses.

Modification Example E

FIG. 29 and FIG. 30 illustrate a modification example of the channel 21 of the contact lens 1 according to the foregoing embodiment. FIG. 29 illustrates an example of an optical path in a state where tears with a low concentration of a detection target substance are accumulated in the channel 21. FIG. 30 illustrates an example of an optical path in a state where tears with a high concentration of the detection target substance are accumulated in the channel 21. It is to be noted that, as illustrated in FIG. 23 and FIG. 24, a difference (a refractive index difference) between a refractive index of the tears and a refractive index of the lens section 10 changes depending on the concentration of the detection target substance included in the tears. Further, as illustrated in FIG. 24, the difference (the refractive index difference) between the refractive index of the tears and the refractive index of the lens section 10 may become substantially zero when the concentration of the detection target substance included in the tears becomes a predetermined concentration.

In the present modification example, at least a portion (e.g., a portion to be irradiated with the irradiation light La) of the channel 21 has a prism shape. At this time, for example, a cross section of at least the portion to be irradiated with the irradiation light La, of the channel 21, is shaped like a right-angled triangle. Further, for example, of the channel 21, a surface S1 corresponding to the hypotenuse of the right-angled triangle is diagonally opposed to a surface on side to be irradiated with the irradiation light La, of the lens section 10. Furthermore, for example, of the channel 21, a surface S2 corresponding to the base of the right-angled triangle is substantially opposed to a surface opposite to the surface on the side to be irradiated with the irradiation light La, of the lens section 10.

When the irradiation light La enters the surface S1 in the state where the tears with the low concentration of the detection target substance are accumulated in the channel 21, for example, as illustrated in FIG. 29, the irradiation light La is refracted by the surface S1 and is also refracted by the surface S2. For this reason, the transmitted light Lb at this time exits in a direction different from a direction of an optical axis of the transmitted light Lb in the state where the tears with the high concentration of the detection target substance are accumulated in the channel 21 (see FIG. 30). This results in a difference in light receiving position in the light receiving section 50, between the state where the tears with the low concentration of the detection target substance are accumulated in the channel 21 and the state where the tears with the high concentration of the detection target substance are accumulated in the channel 21. An amount of this difference varies depending on a magnitude of the refractive index of the tears, which possibly varies depending on the type and the concentration of the component included in the tears. For this reason, in a case where the light receiving section 50 includes, for example, a CCD (Charge Coupled Device) image sensor, a CMOS (Complementary Metal Oxide Semiconductor) image sensor, or the like, the signal processing section 60 is enabled to estimate the type and the concentration of the component included in the tears, on the basis of a position of the transmitted light Lb entering the light receiving section 50.

In this way, in the present modification example, the type and the concentration of the component included in the tears are estimated, not only from the absorption spectrum of the transmitted light Lb but also from an amount of a positional difference (an offset amount) of the transmitted light Lb. This makes it possible to perform analysis with high accuracy.

Modification Example F

FIG. 31 and FIG. 32 illustrate a modification example of the channel 21 of the contact lens 1 according to the above-described modification example A. FIG. 31 illustrates an example of an optical path in a state where tears with a low concentration of a detection target substance are accumulated in the channel 21. FIG. 32 illustrates an example of an optical path in a state where tears with a high concentration of the detection target substance are accumulated in the channel 21. It is to be noted that, as illustrated in FIG. 31 and FIG. 32, the difference (the refractive index difference) between the refractive index of the tears and the refractive index of the lens section 10 changes depending on the concentration of the detection target substance included in the tears. Further, as illustrated in FIG. 32, the difference (the refractive index difference) between the refractive index of the tears and the refractive index of the lens section 10 may become substantially zero when the concentration of the detection target substance included in the tears becomes a predetermined concentration.

In the present modification example, at least a portion (e.g., a portion to be irradiated with the irradiation light La) of the channel 21 has a prism shape. At this time, for example, a cross section of at least the portion to be irradiated with the irradiation light La, of the channel 21, is shaped like a right-angled triangle. Further, for example, of the channel 21, the surface S1 corresponding to the hypotenuse of the right-angled triangle is diagonally opposed to the surface on the side to be irradiated with the irradiation light La, of the lens section 10. Furthermore, for example, of the channel 21, the surface S2 corresponding to the base of the right-angled triangle is substantially opposed to the surface opposite to the surface on the side to be irradiated with the irradiation light La, of the lens section 10.

When the irradiation light La enters the surface S1 in the state where the tears with the low concentration of the detection target substance are accumulated in the channel 21, for example, as illustrated in FIG. 31, the irradiation light La is refracted by the surface S1 and is also refracted by the surface S2. Furthermore, the light refracted and transmitted by the channel 21 is reflected by the reflection layer 22, and refracted by the surfaces S2 and S1 again, and then exits from the surface on the side irradiated with the irradiation light La, as the reflected light Lc.

The reflected light Lc at this time exits in a direction different from a direction of an optical axis of the reflected light Lc in the state where the tears with the high concentration of the detection target substance are accumulated in the channel 21 (see FIG. 32). This results in a difference in light receiving position in the light receiving section 50, between the state where the tears with the low concentration of the detection target substance are accumulated in the channel 21 and the state where the tears with the high concentration of the detection target substance are accumulated in the channel 21. An amount of this difference varies depending on the magnitude of the refractive index of the tears, which possibly varies depending on the type and the concentration of the component included in the tears. For this reason, in a case where the light receiving section 50 includes, for example, a CCD image sensor, a CMOS image sensor, or the like, the signal processing section 60 is enabled to estimate the type and the concentration of the component included in the tears, on the basis of the position of the transmitted light Lb entering the light receiving section 50.

In this way, in the present modification example, the type and the concentration of the component included in the tears are estimated, not only from the absorption spectrum of the transmitted light Lb but also from an amount of a positional difference (an offset amount) of the transmitted light Lb. This makes it possible to perform analysis with high accuracy.

It is to be noted that, in the present modification example, for example, as illustrated in FIG. 33 and FIG. 34, the reflection layer 22 may be formed inside the lens section 10. At this time, the reflection layer 22 may be provided in contact with the surface of the channel 21, or may be provided to be a portion of the inner surface of the channel 21. In such a case, the reflection layer 22 does not touch the eyeball 100, thereby making it possible to reduce the burden on the body further.

Modification Example G

FIG. 35 and FIG. 36 illustrate a modification example of the channel 21 of the contact lens 1 according to the above-described modification example B. FIG. 35 illustrates an example of an optical path in a state where tears with a low concentration of a detection target substance are accumulated in the channel 21. FIG. 36 illustrates an example of an optical path in a state where tears with a high concentration of the detection target substance are accumulated in the channel 21. It is to be noted that, as illustrated in FIG. 35 and FIG. 36, the difference (the refractive index difference) between the refractive index of the tears and the refractive index of the lens section 10 changes depending on the concentration of the detection target substance included in the tears. Further, as illustrated in FIG. 36, the difference (the refractive index difference) between the refractive index of the tears and the refractive index of the lens section 10 may become substantially zero when the concentration of the detection target substance included in the tears becomes a predetermined concentration.

In the present modification example, at least a portion (e.g., a portion to be irradiated with the irradiation light La) of the channel 21 has a prism shape. At this time, for example, a cross section of at least the portion to be irradiated with the irradiation light La, of the channel 21, is shaped like a right-angled triangle. Further, for example, of the channel 21, the surface S1 corresponding to the hypotenuse of the right-angled triangle is diagonally opposed to the surface on the side to be irradiated with the irradiation light La, of the lens section 10. Furthermore, for example, of the channel 21, the surface S2 corresponding to the base of the right-angled triangle is substantially opposed to the surface opposite to the surface on the side to be irradiated with the irradiation light La, of the lens section 10.

When the irradiation light La enters the surface S1 in the state where the tears with the low concentration of the detection target substance are accumulated in the channel 21, for example, as illustrated in FIG. 35, the irradiation light La is diffracted by the diffraction element 23, and further refracted by the surfaces S1 and S1, and then exits from the surface on the side irradiated with the irradiation light La, as the diffracted-transmitted light Ld.

The diffracted-transmitted light Ld at this time exits in a direction different from a direction of an optical axis of the diffracted-transmitted light Ld in the state where the tears with the high concentration of the detection target substance are accumulated in the channel 21 (see FIG. 36). This results in a difference in light receiving position in the light receiving section 50, between the state where the tears with the low concentration of the detection target substance are accumulated in the channel 21 and the state where the tears with the high concentration of the detection target substance are accumulated in the channel 21. An amount of this difference varies depending on the magnitude of the refractive index of the tears, which possibly varies depending on the type and the concentration of the component included in the tears. For this reason, in a case where the light receiving section 50 includes, for example, a CCD image sensor, a CMOS image sensor, or the like, the signal processing section 60 is enabled to estimate the type and the concentration of the component included in the tears, on the basis of the position of the diffracted-transmitted light Ld entering the light receiving section 50.

In this way, in the present modification example, the type and the concentration of the component included in the tears are estimated, not only from the absorption spectrum of the diffracted-transmitted light Ld but also from an amount of a positional difference (an offset amount) of the diffracted-transmitted light Ld. This makes it possible to perform analysis with high accuracy.

It is to be noted that, in the present modification example, for example, as illustrated in FIG. 37 and FIG. 38, the diffraction element 23 may be formed inside the lens section 10. At this time, the diffraction element 23 may be provided in contact with the surface of the channel 21, or may be provided to be a portion of the inner surface of the channel 21. In such a case, the diffraction element 23 does not touch the eyeball 100, thereby making it possible to reduce the burden on the body further.

Modification Example H

FIG. 39 and FIG. 40 illustrate a modification example of the channel 21 of the contact lens 1 according to the above-described modification example C. FIG. 39 illustrates an example of an optical path in a state where tears with a low concentration of a detection target substance are accumulated in the channel 21. FIG. 40 illustrates an example of an optical path in a state where tears with a high concentration of the detection target substance are accumulated in the channel 21. It is to be noted that, as illustrated in FIG. 39 and FIG. 40, the difference (the refractive index difference) between the refractive index of the tears and the refractive index of the lens section 10 changes depending on the concentration of the detection target substance included in the tears. Further, as illustrated in FIG. 40, the difference (the refractive index difference) between the refractive index of the tears and the refractive index of the lens section 10 may become substantially zero when the concentration of the detection target substance included in the tears becomes a predetermined concentration.

In the present modification example, at least a portion (e.g., a portion to be irradiated with the irradiation light La) of the channel 21 has a prism shape. At this time, for example, a cross section of at least the portion to be irradiated with the irradiation light La, of the channel 21, is shaped like a right-angled triangle. Further, for example, of the channel 21, the surface S1 corresponding to the hypotenuse of the right-angled triangle is diagonally opposed to the surface on the side to be irradiated with the irradiation light La, of the lens section 10. Furthermore, for example, of the channel 21, the surface S2 corresponding to the base of the right-angled triangle is substantially opposed to the surface opposite to the surface on the side to be irradiated with the irradiation light La, of the lens section 10. The reflection layer 22 and the diffraction element 23 are disposed to be opposed to each other, with at least the portion having the prism shape of the channel 21 interposed therebetween.

When the irradiation light La enters the surface S1 in the state where the tears with the low concentration of the detection target substance are accumulated in the channel 21, for example, as illustrated in FIG. 39, the irradiation light La is diffracted by the diffraction element 23, and further refracted by the surfaces S1 and S2. Further, the light refracted and transmitted by the channel 21 is reflected by the reflection layer 22 and refracted by the surfaces S2 and S1 again, and then exists from the surface on the side irradiated with the irradiation light La, as the diffracted-reflected light Le.

The diffracted-reflected light Le at this time exits in a direction different from a direction of an optical axis of the diffracted-reflected light Le in the state where the tears with the high concentration of the detection target substance are accumulated in the channel 21 (see FIG. 40). This results in a difference in light receiving position in the light receiving section 50, between the state where the tears with the low concentration of the detection target substance are accumulated in the channel 21 and the state where the tears with the high concentration of the detection target substance are accumulated in the channel 21. An amount of this difference varies depending on the magnitude of the refractive index of the tears, which possibly varies depending on the type and the concentration of the component included in the tears. For this reason, in a case where the light receiving section 50 includes, for example, a CCD image sensor, a CMOS image sensor, or the like, the signal processing section 60 is enabled to estimate the type and the concentration of the component included in the tears, on the basis of the position of the diffracted-reflected light Le entering the light receiving section 50.

It is possible to perform measurement of the component of the tears accumulated in the contact lens 1 according to the present modification example, using, for example, the measurement device 2 illustrated in each of FIG. 22, FIG. 25, FIG. 27, and FIG. 28. At this time, the light receiving section 50 detects the light (the diffracted-reflected light Le) diffracted by the diffraction element 23, refracted by the portion having the prism shape of the channel 21, transmitted by the tears accumulated in the one or plurality of structure portions 20, reflected by the reflection layer 22, and refracted by the portion having the prism shape of the channel 21 again, and further transmitted by the accumulated tears as well as being diffracted by the diffraction element 23, of the light (the irradiation light La) emitted toward the tears accumulated in the one or plurality of structure portions 20. The light receiving section 50 outputs the detection signal generated by receiving the diffracted-reflected light Le to the signal processing section 60. The signal processing section 60 analyzes the inputted detection signal, and determines the state of the living body using, for example, the above-described analysis method. It is to be noted that, when using the measurement device 2 illustrated in each of FIG. 25, FIG. 27, and FIG. 28, it is possible to measure the component of the tears, in the state where the contact lens 1 according to the present modification example is attached to the eyeball 100.

In this way, in the present modification example, the type and the concentration of the component included in the tears are estimated, not only from the absorption spectrum of the diffracted-reflected light Le but also from an amount of a positional difference (an offset amount) of the diffracted-reflected light Le. This makes it possible to perform analysis with high accuracy.

It is to be noted that, in the present modification example, for example, as illustrated in FIG. 41 and FIG. 42, the reflection layer 22 and the diffraction element 23 may be formed inside the lens section 10. At this time, the reflection layer 22 may be provided in contact with the surface of the channel 21, or may be provided to be a portion of the inner surface of the channel 21. In such a case, the reflection layer 22 and the diffraction element 23 do not touch the eyeball 100, thereby making it possible to reduce the burden on the body further.

Modification Example I

FIG. 43 and FIG. 44 illustrate a modification example of the structure portion 20 of the contact lens 1 according to each of the foregoing embodiment and the modification examples A to H thereof. FIG. 43 illustrates a configuration example of a horizontal cross section of the channel 21. FIG. 44 illustrates a configuration example of a vertical cross section of the channel 21.

In the present modification example, the one or plurality of structure portions 20 includes a suction chamber 21C coupled to the channel 21 (the outlet 21B). In other words, the outlet 21B is not exposed on the surface of the lens section 10. Further, the one or plurality of structure portions 20 includes a sealing section 24 that seals an inlet 21f of the channel 21. The suction chamber 21C is filled with gas of pressure lower than atmospheric pressure. Coupling between the suction chamber 21C and outside air is blocked by the sealing section 24. The sealing section 24 includes, for example, a material dissolvable by the tears. For this reason, when the contact lens 1 is attached to the eyeball 100, the sealing section 24 is dissolved by the tears, and the suction chamber 21C communicates with the outside air. As a result, the tears are drawn into the suction chamber 21C through the channel 21, and accumulated in the channel 21 and the suction chamber 21C. It is to be noted that a cover material not to be dissolved by tears may be provided between the sealing section 24 and the inlet 21f. The cover material is detached from the inlet 21f by the dissolution of the sealing section 24 by the tears. It is to be noted that the inlet 21A may be exposed on the surface on the side to be in contact with the eyeball 100, of the lens section 10, or may be exposed on the surface on the side not to be in contact with the eyeball 100. The entrance 21A is, for example, disposed at a position close to the edge of the lens section 10, in the channel 21. In other words, the inlet 21A is, for example, disposed at a position close to the lacrimal gland when the contact lens 1 is attached to the eyeball 100.

In this way, in the present modification example, the tears are accumulated in the channel 21 and the suction chamber 21C by the dissolution of the sealing section 24. This makes it possible to, for example, measure the absorption spectrum of the tears with accuracy. Here, because the light does not pass through a large-absorption region such as skin when the light is emitted toward the tears, it is possible to, for example, measure the absorption spectrum of the tears easily. Further, it is easy to separate noise and a signal of a detection target. Furthermore, because an electrode is unnecessary, issues such as long-term stability and heat resistance attributable to an electrode, and responsiveness to a substance other than a detection target, are not present. Moreover, because this is of the non-invasive type, a burden on a body is small. It is therefore possible to perform analysis with high accuracy while keeping a burden on a body small.

Modification Example J

FIG. 45 illustrates a modification example of the structure portion 20 of the contact lens 1 according to the above-described modification example I. FIG. 45 illustrates a configuration example of a horizontal cross section of the channel 21.

In the present modification example, the one or plurality of structure portions 20 includes a plurality of storage chambers 25 coupled to the channel 21 (the outlet 21B). Each of the storage chambers 25 and the channel 21 are coupled by a coupling channel 25A narrower than the storage chamber 25. Coupling positions of the respective coupling channels 25A with respect to the channel 21 vary. Distances of the respective coupling channels 25A from the inlet 21A are therefore different from each other. Here, the channel 21 may be subjected to a water-repellent treatment. Further, each of the storage chambers 25 may include a material (a reaction material 26) that develops color or displays fluorescence by enzymatic reaction or chemical reaction with the tears. The reaction material 26 includes, for example, oxygen, and causes the following reaction with glucose included in the tears. In the following reaction, a quinone pigment with largest absorption at a wavelength of 558 nm is generated. It is possible to detect a glucose concentration by measuring absorption of this quinone pigment at a wavelength of 550 nm.

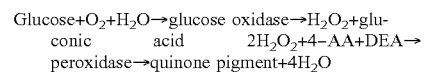

Glucose+$O_2$+$H_2O$→glucose oxidase→$H_2O_2$+gluconic acid  2$H_2O_2$+4-AA+DEA→peroxidase→quinone pigment+4$H_2O$ Further, because the coupling positions of the respective coupling channels 25A with respect to the channel 21 vary, a time during which the reaction material 26 reacts with the tears is different for each of the storage chambers 25. This makes it possible to estimate a change with time of the component included in the tears by detecting a reaction state of the reaction material 26, for each of the storage chambers 25. It is to be noted that a reaction time of the reaction material 26 in each of the storage chambers 25 is adjustable by adjusting a negative pressure, etc. of the suction chamber 21C.

Further, in a case where each of the coupling channels 25A is subjected to the water-repellent treatment, when the negative pressure of the suction chamber 21C is released, and an inflow of the tears into the channel 21 is stopped, the tears collected in the channel 21 and the tears collected in each of the storage chambers 25 (a liquid in a state of color development or fluorescence display) are spatially separated from each other by a water-repellent effect of each of the coupling channels 25A. This makes it possible to prevent the tears collected in each of the storage chambers 25 (the liquid in the state of color development or fluorescence display) from flowing into the channel 21 and thereby mixing with tears collected in the other storage chambers 25.

Modification Example J

FIG. 46 illustrates a modification example of the glasses 4 used in the above-described modification example C. FIG. 46 illustrates an example in which a medicinal-solution supply device 5 is provided in the temple 42. For example, when the user wears the glasses 4, a needle provided in the medicinal-solution supply device 5 sticks in the user, and the medicinal-solution supply device 5 supplies the user with, for example, a medicinal solution such as insulin. The measurement device 2 is enabled to monitor, in real time, an effect of the medicinal solution supplied to the user, by analyzing the component of the tears.

3. Second Embodiment

[Configuration]

A contact lens 3 according to a second embodiment of the present disclosure is described. FIG. 47 illustrates an example of a state where the contact lens 3 is attached to the eyeball 100. FIG. 48 illustrates an example of a cross-sectional configuration of the contact lens 3 and the eyeball 100. The contact lens 3 includes the lens section 10 attachable to the eyeball 100, and one or a plurality of structure portions 80 provided in the lens section 10. The one or plurality of structure portions 80 is a structure that accumulates tears, and further a structure that guides external light to the pupil 120 or the iris 110.

The one or plurality of structure portions 80 is formed, for example, to avoid the middle of the lens section 10. The one or plurality of structure portions 80 is formed, for example, as illustrated in FIG. 48, to avoid a point opposed to a middle of the pupil 120, when the contact lens 3 is attached to the eyeball 100. In the one or plurality of structure portions 80, one end is disposed at a position close to an end portion of the lens section 10, and another end is disposed at an edge of the pupil 120 or the iris 110, when the contact lens 3 is attached to the eyeball 100. It is to be noted that the one or plurality of structure portions 80 may be provided only at the middle of the lens section 10, or may be provided in a region including the middle of the lens section 10. In the one or plurality of structure portions 80, one end may be disposed at a position close to the end portion of the lens section 10, and another end may be disposed at the middle of the pupil 120 or the iris 110, when the contact lens 3 is attached to the eyeball 100.

The one or plurality of structure portions 80 includes, for example, a channel 81 provided inside the lens section 10. The channel 81 has, for example, a cylindrical shape extending in a direction parallel to the surface of the lens 10, as illustrated in FIG. 48. A cross-section shape of the channel 21 is, for example, a rectangular shape, a polygonal shape, a circular shape, or an elliptical shape. It is to be noted that a case where the cross-section shape of the channel 21 is a rectangular shape is exemplified in FIG. 49 and FIG. 50. It is to be noted that, in a case where the lens section 10 is provided with the plurality of structure portions 80 (i.e., the plurality of channels 81), the plurality of structure portions 80 (i.e., the plurality of channels 81) may be disposed at respective positions opposed to each other with the middle of the lens section 10 interposed therebetween. For example, in a case where the two structure portions 80 (i.e., the two channels 81) are provided in the lens section 10, the two structures portions 80 (i.e., the two channels 81) may be disposed at respective positions opposed to each other with the middle of the lens section 10 interposed therebetween.

The channel 81 includes, for example, an opening 81A serving as an inlet for the tears, and an opening 81B serving as an outlet for the tears, as illustrated in FIG. 48, FIG. 49, and FIG. 50. The opening 81A is exposed, for example, on the surface on the side to be in contact with the eyeball 100, of the lens section 10. The opening 81B is exposed, for example, on the surface on the side not to be in contact with the eyeball 100, of the lens section 10. The opening 81A is, for example, disposed at a position close to the edge of the lens section 10, in the channel 81. It is preferable that, of the channel 81, a point (an inflow path) relatively close to the opening 81A have, for example, a width that makes it possible to draw the tears in by the capillary phenomenon. It is preferable that, of the channel 81, a point (a discharge path) relatively close to the opening 81B have, for example, a width wider than that of the point relatively close to the opening 81A, of the channel 81. It is to be noted that, of the channel 81, the point (the discharge path) relatively close to the opening 81B may have a width equal to that of the point relatively close to the opening 81A, of the channel 81. Of the channel 81, the width of the point relatively close to the opening 81B has a distance that, for example, makes it difficult to cause the capillary phenomenon. A portion or whole of the channel 81 may be subjected to, for example, a hydrophilic treatment to make the tears flow easily.

The one or plurality of structure portions 80 includes a reaction material 82 being in contact with an inner surface of the channel 81. The reaction material 82 is provided as a thin layer on the inner surface of the channel 81 to the extent of not blocking the channel 81. The reaction material 82 includes, for example, a material that develops color or displays fluorescence by enzymatic reaction or chemical reaction with the tears. The reaction material 82 includes, for example, oxygen, and causes the following reaction with glucose included in the tears. In the following reaction, a quinone pigment with largest absorption at a wavelength of 558 nm is generated. At this time, a glucose concentration is detected by color of external light L transmitted by a solution in which this quinone pigment is dissolved. It is to be noted that the reaction material 82 is not limited to the above-described material, and is allowed to include a material appropriate for a detection target. The reaction material 82 may include other material, and may include, for example, a boronic acid. Examples of the boronic acid include phenylboronic acid, anthrylboronic acid, aromatic boronic acid, arylboronic acid, $ArB(OH)_2$, etc.

Glucose+$O_2$+$H_2O$→glucose oxidase→$H_2O_2$+gluconic acid    $2H_2O_2$+4–AA+DEA→peroxidase→quinone pigment+$4H_2O$ The one or plurality of structure portions 80 includes a reflecting mirror 81C that guides the external light L entering through the opening 81B to inside of the channel 81, and a reflecting mirror 81D that reflects the external light L propagating through the inside of the channel 81 to the pupil 120 or the iris 110 through the opening 81A. The reflecting mirror 81C is disposed to cause multiple reflection of the light reflected by the reflecting mirror 81C, on the inner surface of the channel 81. It is to be noted that a case where the reflecting mirror 81C is disposed to cause the multiple reflection of the light reflected by the reflecting mirror 81C on upper and lower surfaces of the inner surface of the channel 81 is exemplified in FIG. 49. Further, a case where the reflecting mirror 81C is disposed to cause the multiple reflection of the light reflected by the reflecting mirror 81C on right and left surfaces of the inner surface of the channel 81 is exemplified in FIG. 50.

It is to be noted that, for example, as illustrated FIG. 51, a diffraction element 83 that guides the external light L to the inside of the channel 81 may be provided in place of the reflecting mirror 81C. Further, for example, as illustrated in FIG. 51, a diffraction element 84 that guides the external light L propagating through the inside of the channel 81 to the pupil 120 or the iris 110 through the opening 81A may be provided in place of the reflecting mirror 81D. The diffraction element 83 is configured to allow refraction of the external light L entering through the opening 81B in a predetermined direction in the inside of the channel 81, and includes, for example, a holo-graphic optical element (HOE). The diffraction element 84 is configured to allow refraction of the light propagating through the inside of the channel 81 in a direction to the opening 81A, and includes, for example, a holo-graphic optical element (HOE).

In this way, by causing the multiple reflection in the inside of the channel 81, it is possible to increase a propagating distance of the external light L propagating through the inside of the channel 81, as compared with a case where the external light L is perpendicularly transmitted by the channel 81. For example, suppose the channel 81 has a height (a thickness) of 0.1 mm, and a length of 4 mm. At this time, in a case where the external light L is perpendicularly transmitted by the channel 81, a distance in which the external light L passes through the inside of the channel 81 is only 0.1 mm. In contrast, in a case where the external light L propagates through the inside of the channel 81 at an internal reflection of 45 degrees, the distance in which the external light L passes through the inside of the channel 81 is about 5.6 mm. This makes it possible to increase a proportion (an absorption factor) of the external light L to be absorbed by a light absorption material generated by the reaction between the tears and the reaction material 82.

Here, an intensity of light propagating through inside of a dilute solution in which a light absorption material is dissolved is proportional to a concentration of the light absorption material included in the dilute solution and a distance in which the light passes through the inside of the dilute solution, from the Lambert-Beer's law. For this reason, as the channel 81 is longer, an amount of light absorption of the external light L by the solution in which the light absorption material is dissolved, i.e., a degree of a change in color of the external light L transmitted by the channel 81, is larger. For example, suppose the channel 81 has a height (a thickness) of 0.1 mm, and a length of 4 mm. Further, suppose the reaction material 82 includes a glucose E reagent. At this time, in the case where the external light L is perpendicularly transmitted by the channel 81, a proportion (a transmittance) of a component of a wavelength of 505 nm included in the external light L transmitted by the channel 81 is 99.99959. In this case, visually recognizing a change in the color of the external light L transmitted by the channel 81 is difficult. In contrast, in the case where the external light L propagates through the inside of the channel 81 at the internal reflection of 45 degrees, the proportion (the transmittance) of the component of the wavelength of 505 nm included in the external light L transmitted by the channel 81 is 82.4%. If the transmittance falls to this extent, it is possible to easily perform visual recognition of a change in the color of the external light L transmitted by the channel 81. In other words, in this case, it is possible to discriminate a change in blood sugar level by viewing the change.

It is to be noted that, in a case where the reaction material 82 is a material or in a form that does not dissolve in the tears, as the number of times the external light L is reflected by a surface of the reaction material 82 within the channel 81 is larger, the amount of light absorption of the external light L by the reaction material 82, i.e., the degree of a change in the color of the external light L transmitted by the channel 81, is larger. At this time, it is possible to lower a proportion (a transmittance) of a component of a predetermined wavelength included in the external light L transmitted by the channel 81 to the extent that it is possible to easily perform visual recognition of a change in the color of the external light L, as described above. In other words, in this case as well, it is possible to discriminate a change in blood sugar level by viewing the change.

Next, an example of a judgement procedure for a state of a living body using the contact lens 3 is described. FIG. 52 illustrates an example of the judgement procedure for the state of the living body using the contact lens 3. First, the user attaches the contact lens 3 to the eyeball 100 of the user (step S301). Then, the tears are accumulated in the one or plurality of structure portions 80 (the channel 81) provided in the contact lens 3 by utilizing, for example, the capillary phenomenon.

At this time, the reaction material 82 reacts with the tears (step S302). As a result, the light absorption material is generated, and the channel 81 is filled with the dilute solution in which the light absorption material is dissolved in the tears. Here, the concentration of the light absorption material included in the tears changes depending on an amount of the component reacting with the reaction material 82, included in the tears. In a case where the reaction material 82 includes the glucose E reagent, for example, a quinone pigment is generated by the reaction between the reaction material 82 and the tears, and the channel 81 is filled with a dilute solution in which the quinone pigment is dissolved in the tears.

Next, the user observes the light outputted from the one or plurality of structure portions 80 (the channel 81) provided in the contact lens 3, and determines the state of the living body on the basis of the color of the light (step S303). At this time, when the external light L enters the one or plurality of structure portions 80 (the channel 81), the external light L is absorbed by the light absorption material included in the above-described dilute solution. Here, the amount of light absorption of the external light L by the dilute solution in which the light absorption material is dissolved, i.e., the degree of a change in the color of the external light L transmitted by the channel 81, is proportional to the concentration of the light absorption material included in the dilute solution and the distance in which the external light L passes through the inside of the dilute solution. This enables the user to determine the state of the living body on the basis of the color of the light outputted from the one or plurality of structure portions 80 (the channel 81) provided in the contact lens 3.

[Effects]

In the present embodiment, the one or plurality of channels 81 is provided with a reflecting mirror 81B or the diffraction element 83 that guides the external light L to the inside of the channel 81, and a reflecting mirror 81A or the diffraction element 84 that guides the external light L propagating through the inside of the channel 81 to the pupil 120 or the iris 110, and is further provided with the reaction material 82 within the channel 81. This enables the user to judge the state of the living body simply and in real time by observing the color of the light outputted from the one or plurality of structure portions 80 (the channel 81) while the contact lens 1 remains attached to the eyeball 100. As a result, for example, it is possible for the user to judge the state of the living body simply and in real time even while the user is carrying out any activity, and thus, in a case where the user suffers from diabetes, the user is enabled to judge instantly whether it is necessary to inject insulin now. Further, because an electrode is unnecessary, issues such as long-term stability and heat resistance attributable to an electrode, and responsiveness to a substance other than a detection target, are not present. Moreover, because this is of the non-invasive type, a burden on a body is small. It is therefore possible to perform analysis with high accuracy while keeping a burden on a body small.

4. Modification Examples of Second Embodiment

In the second embodiment, for example, as illustrated in FIG. 53, the contact lens 3 may include a color index 90. The color index 90 is a color sample intended for comparison with the color of the light outputted from the one or plurality of structure portions 20 (the channel 81) provided in the contact lens 3. When the contact lens 3 is attached to the eyeball 100, the color index 90 is provided, for example, in proximity to the edge of the pupil 120 or the iris 110. In such a case, the user is enabled to judge the state of the living body instantly and accurately by comparing the color of the light outputted from the one or plurality of structure portions 80 (the channel 81) and the color index 90.

It is to be noted that, for example, as illustrated in FIG. 54(A) and FIG. 54(B), the color index 90 may be disposed to be adjacent to the structure portion 80 (in particular, the opening 81B). It is to be noted that a plane configuration of the one or plurality of structure portions 80 and the color index 90 is exemplified in FIG. 54(A). Further, a cross-sectional configuration at a line A-A in FIG. 54(A) is exemplified in FIG. 54(B). In such a case, the user is enabled to perform the comparison between the color of the light outputted from the opening 81B and the color index 90 more accurately.

Further, for example, as illustrated in FIG. 54(B), the color index 90 may be provided in contact with a surface 3A on the eyeball 100 side, of the lens 10. In such a case, it is possible to prevent the color index 90 from being changed in color by the external light L when the user visually recognizes the color index 90. As a result, the user is enabled to perform the comparison between the color of the light outputted from the structure portion 80 (the channel 81) and the color index 90 more accurately.

It is to be noted that, as illustrated in FIG. 55, the plurality of structure portions 80 (in particular, the opening 81B) and the plurality of color indexes 90 may be disposed to be alternately aligned in a predetermined direction. It is to be noted that a plane configuration of the plurality of structure portions 80 and the plurality of color indexes 90 is exemplified in FIG. 55. In such a case, the user is enabled to perform the comparison between the color of the light outputted from the opening 81B and the color index 90 more accurately.

Further, as illustrated in FIG. 56 (A) and FIG. 56 (B), in a case where the one structure portion 80 is formed to have a wide width, the plurality of color indexes 90 may be disposed to block a portion of the opening 81B. It is to be noted that a plane configuration of the one structure portion 80 and the plurality of color indexes 90 is exemplified in FIG. 56 (A). Furthermore, a cross-sectional configuration at a line A-A in FIG. 56 (A) is exemplified in FIG. 56 (B). In such a case, the user is enabled to perform the comparison between the color of the light outputted from the opening 81B and the color index 90 more accurately.

Further, as illustrated in FIG. 57, in a case where the plurality of structure portions 80 (in particular, the opening 81B) and the plurality of color indexes 90 are disposed to be alternately aligned in a predetermined direction, each of the color indexes 90 may extend in an extending direction of the structure portion 80. In such a case, the user is enabled to visually recognize each of the color indexes 90 clearly, and thus is enabled to perform the comparison between the color of the light outputted from the opening 81B and the color index 90 more accurately.

Further, in the second embodiment, for example, as illustrated in FIG. 58, the one or plurality of structure portions 80 may include a sealing layer 85 that seals the opening 81B, and a sealing layer 86 that seals the opening 81A. The sealing sections 85 and 86 each include, for example, a material dissolvable by the tears. For this reason, when the contact lens 3 is attached to the eyeball 100, the sealing sections 85 and 86 are dissolved by the tears, and the channel 81 communicates with the outside air. As a result, the tears are drawn into the channel 81. Here, in a case where the contact lens 3 is provided with the plurality of structure portions 80 such as those illustrated in FIG. 54, a dissolution rate of the sealing sections 85 and 86 may be different for each of the structure portions 80. In such a case, a time during which the reaction material 82 reacts with the tears is different for each of the structure portions 80. This makes it possible to estimate a change with time of the state of the living body by observing the color of the light outputted from the structure portion 80, for each of the structure portions 80.

Although the present disclosure has been described above referring to the embodiments and modification examples, the present disclosure is not limited thereto, and may be modified in a variety of ways.

For example, the glasses 4 used in the above-described modification example C or the above-described modification example J may include an element (e.g., a gyro element) that detects a posture of a person. The signal processing device 60 is enabled to evaluate the detection signal obtained from the light receiving section 50, on the basis of information obtained from the element that detects the posture of the person.

Further, for example, in the foregoing embodiments and the modification examples thereof, in a case where an evaluation result obtained from the light receiving section 50 matches with a predetermined state, the signal processing device 60 may perform display and/or sound output for an alert.

It is to be noted that the effects described in the present specification are merely examples. The effects of the present disclosure are not limited to those described in the present specification. The present disclosure may include effects other than those described in the present specification.

Further, for example, the present disclosure may have the following configurations.

(1)

A contact lens including:
a lens section attachable to an eyeball; and
one or a plurality of structure portions intended to accumulate tears.

(2)

The contact lens according to (1), in which the one or plurality of structure portions is formed to avoid a middle of the lens section.

(3)

The contact lens according to (1) or (2), in which the one or plurality of structure portions includes a channel provided inside the lens section.

(4)

The contact lens according to (3), in which the channel includes an inflow path enabled to draw tears in by a capillary phenomenon.

(5)

The contact lens according to (4), in which the channel includes a discharge path having a width wider than a width of the inflow path.

(6)

The contact lens according to (4) or (5), in which an entrance of the inflow path is disposed at a position close to an edge of the lens section, in the channel.

(7)

The contact lens according to any one of (3) to (6), in which the one or plurality of structure portions further includes a sealing section that includes a material dissolvable by tears and seals an inlet of the channel.

(8)

The contact lens according to (7), in which the one or plurality of structure portions further includes a suction chamber coupled to the channel.

(9)

The contact lens according to (8), in which the one or plurality of structure portions further includes a plurality of storage chambers that is coupled to the channel and stores tears.

(10)

The contact lens according to (9), in which the channel is subjected to a water-repellent treatment.

(11)

The contact lens according to (10), in which each of the storage chambers includes a material that develops color or displays fluorescence by enzymatic reaction or chemical reaction with tears.

(12)

The contact lens according to any one of (3) to (11), in which the plurality of structure portions is disposed at respective positions opposed to each other with a middle of the lens section interposed therebetween.

(13)

The contact lens according to any one of (3) to (12), in which the one or plurality of structure portions further includes a diffraction element disposed to be opposed to the channel in a thickness direction of the lens section.

(14)

The contact lens according to (13), in which the one or plurality of structure portions further includes a reflection layer disposed to be opposed to the channel in the thickness direction of the lens section.

(15)

The contact lens according to any one of (3) to (12), in which
at least a portion of the channel has a prism shape, and
the one or plurality of structure portions further includes a reflection layer and a diffraction element disposed to be opposed to each other with at least the portion having the prism shape of the channel interposed therebetween.

(16)

The contact lens according to any one of (3) to (12), in which the one or plurality of structure portions further includes a reflection layer disposed to be opposed to the channel in a thickness direction of the lens section.

(17)

A detection method including:
emitting light toward tears accumulated in one or a plurality of structure portions in a contact lens that includes a lens section attachable to an eyeball, and the one or plurality of structure portions intended to accumulate tears; and
detecting, through the tears accumulated in the one or plurality of structure portions, transmitted light transmitted by the contact lens, reflected light reflected by the contact lens, diffracted-transmitted light diffracted and transmitted by the contact lens, or diffracted-reflected light diffracted and reflected by the contact lens, of the light emitted toward the tears accumulated in the one or plurality of structure portions.

(18)

The detection method according to (17), in which
the one or plurality of structure portions further includes a reflection layer disposed to be opposed to the channel in a thickness direction of the lens section, and
the measurement method further includes detecting the reflected light transmitted by the tears accumulated in the one or plurality of structure portions, and reflected by the reflection layer, of the light emitted toward the tears accumulated in the one or plurality of structure portions.

(19)

The detection method according to (17), in which
the one or plurality of structure portions further includes a diffraction element disposed to be opposed to the channel in a thickness direction of the lens section, and
the measurement method further includes detecting the diffracted-transmitted light diffracted by the diffraction element, and transmitted by the tears accumulated in the one or plurality of structure portions, of the light emitted toward the tears accumulated in the one or plurality of structure portions.

(20)

The detection method according to (17), in which
the one or plurality of structure portions further includes a diffraction element disposed to be opposed to the channel in a thickness direction of the lens section, and a reflection layer disposed to be opposed to the diffraction element with the channel interposed therebetween,
of the channel, at least a portion opposed to the diffraction element has a prism shape, and
the measurement method further includes detecting the diffracted-reflected light diffracted by the diffraction element, refracted by the portion having the prism shape of the channel, transmitted by the tears accumulated in the one or plurality of structure portions, and reflected by the reflection layer, of the light emitted toward the tears accumulated in the one or plurality of structure portions.

(21)
The contact lens according to (6), in which
the entrance of the inflow path and an exit of the discharge path are disposed at respective positions that have left-right symmetry with respect to a middle of the lens section, and
the entrance and the exit are configured to have the entrance be disposed at a position relatively close to a lacrimal gland as compared with the exit, in the structure portion relatively close to the lacrimal gland when the contact lens is attached to the eyeball.

(22)
The contact lens according to (13), in which the diffraction element is provided inside the lens section.

(23)
The contact lens according to (14), in which the reflection layer is provided inside the lens section.

(24)
The contact lens according to (3), in which at least a portion of the channel has a prism shape.

(25)
The contact lens according to (24), in which the one or plurality of structure portions further includes a reflection layer disposed to be opposed to the portion having the prism shape of the channel in a thickness direction of the lens section.

(26)
The contact lens according to (24), in which the one or plurality of structure portions further includes a diffraction element disposed to be opposed to the portion having the prism shape of the channel in a thickness direction of the lens section.

(27)
The contact lens according to (25), in which the one or plurality of structure portions further includes a diffraction element disposed to be opposed to the portion having the prism shape of the channel in the thickness direction of the lens section.

(28)
The detection method according to (17), in which the one or plurality of structure portions further includes a diffraction element disposed to be opposed to the channel in a thickness direction of the lens section, and a reflection layer disposed to be opposed to the diffraction element with the channel interposed therebetween, and
the measurement method further includes detecting the diffracted-reflected light diffracted by the diffraction element, transmitted by the tears accumulated in the one or plurality of structure portions, and reflected by the reflection layer, of the light emitted toward the tears accumulated in the one or plurality of structure portions.

(29)
The detection method according to (17), in which
the diffraction element is disposed at a position farther from the eyeball than the channel is when the contact lens is attached to the eyeball,
the reflection layer is disposed at a position closer to the eyeball than the channel is when the contact lens is attached to the eyeball, and
the measurement method further includes detecting the diffracted-reflected light diffracted by the diffraction element, transmitted by the tears accumulated in the one or plurality of structure portions, and reflected by the reflection layer, of the light emitted toward the tears accumulated in the one or plurality of structure portions, in a state where the contact lens is attached to the eyeball.

(30)
The detection method according to (17), in which in the measurement method, an absorption spectrum of tears is derived on a basis of a detection signal obtained by detecting the transmitted light, the reflected light, the diffracted-transmitted light, or the diffracted-reflected light, and a type and a concentration of a component included in the tears is estimated from the derived absorption spectrum.

(31)
The contact lens according to any one of (1) to (6), in which the one or plurality of structure portions further includes
a first optical element that guides external light to inside of the channel,
a second optical element that guides the external light propagating through the inside of the channel to a pupil or an iris, and
a reaction material provided in the inside of the channel, the reaction material developing color or displaying fluorescence by enzymatic reaction or chemical reaction with tears.

This application claims the benefit of Japanese Priority Patent Application JP2017-150559 filed with the Japan Patent Office on Aug. 3, 2017, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. A contact lens comprising:
a lens section attachable to an eyeball; and
one or a plurality of structure portions provided in the lens section and intended to accumulate tears,
wherein the one or plurality of structure portions includes an inlet coupled with an inflow path and an outlet coupled with a discharge path, and the inlet is adjacent to an outer edge of the lens and the outlet is provided in an area between a pupil and an iris.

2. The contact lens according to claim 1, wherein the one or plurality of structure portions is formed to avoid a middle of the lens section.

3. The contact lens according to claim 2, wherein the one or plurality of structure portions includes a channel provided inside the lens section.

4. The contact lens according to claim 3, wherein the channel includes an inflow path enabled to draw tears in by a capillary phenomenon.

5. The contact lens according to claim 4, wherein the channel includes a discharge path having a width wider than a width of the inflow path.

6. The contact lens according to claim 4, wherein an entrance of the inflow path is disposed at a position close to an edge of the lens section, in the channel.

7. The contact lens according to claim 3, wherein the one or plurality of structure portions further includes a sealing section that includes a material dissolvable by tears and seals an inlet of the channel.

8. The contact lens according to claim 7, wherein the one or plurality of structure portions further includes a suction chamber coupled to the channel.

9. The contact lens according to claim 8, wherein the one or plurality of structure portions further includes a plurality of storage chambers that is coupled to the channel and stores tears.

10. The contact lens according to claim 9, wherein the channel is subjected to a water-repellent treatment.

11. The contact lens according to claim 10, wherein each of the storage chambers includes a material that develops color or displays fluorescence by enzymatic reaction or chemical reaction with tears.

12. The contact lens according to claim 1, wherein the one or plurality of structure portions further includes
a first optical element that guides external light to inside of the channel,
a second optical element that guides the external light propagating through the inside of the channel to a pupil or an iris, and
a reaction material provided in the inside of the channel, the reaction material developing color or displaying fluorescence by enzymatic reaction or chemical reaction with tears.

13. The contact lens according to claim 3, wherein the one or plurality of structure portions further includes a diffraction element disposed to be opposed to the channel in a thickness direction of the lens section.

14. The contact lens according to claim 13, wherein the one or plurality of structure portions further includes a reflection layer disposed to be opposed to the channel in the thickness direction of the lens section.

15. The contact lens according to claim 3, wherein
at least a portion of the channel has a prism shape, and
the one or plurality of structure portions further includes a reflection layer and a diffraction element disposed to be opposed to each other with at least the portion having the prism shape of the channel interposed therebetween.

16. The contact lens according to claim 3, wherein the one or plurality of structure portions further includes a reflection layer disposed to be opposed to the channel in a thickness direction of the lens section.

17. A detection method comprising:
emitting light toward tears accumulated in one or a plurality of structure portions in a contact lens that includes a lens section attachable to an eyeball, and the one or plurality of structure portions provided in the lens section and intended to accumulate tears, wherein the one or plurality of structure portions includes an inlet coupled with an inflow path and an outlet coupled with a discharge path, and the inlet is adjacent to an outer edge of the lens and the outlet is provided in an area between a pupil and an iris; and
detecting, through the tears accumulated in the one or plurality of structure portions, transmitted light transmitted by the contact lens, reflected light reflected by the contact lens, diffracted-transmitted light diffracted and transmitted by the contact lens, or diffracted-reflected light diffracted and reflected by the contact lens, of the light emitted toward the tears accumulated in the one or plurality of structure portions.

18. The detection method according to claim 17, wherein the one or plurality of structure portions further includes
a reflection layer disposed to be opposed to the channel in a thickness direction of the lens section, and
the measurement method further includes detecting the reflected light transmitted by the tears accumulated in the one or plurality of structure portions, and reflected by the reflection layer, of the light emitted toward the tears accumulated in the one or plurality of structure portions.

19. The detection method according to claim 17, wherein the one or plurality of structure portions further includes
a diffraction element disposed to be opposed to the channel in a thickness direction of the lens section, and
the measurement method further includes detecting the diffracted-transmitted light diffracted by the diffraction element, and transmitted by the tears accumulated in the one or plurality of structure portions, of the light emitted toward the tears accumulated in the one or plurality of structure portions.

20. The detection method according to claim 17, wherein the one or plurality of structure portions further includes
a diffraction element disposed to be opposed to the channel in a thickness direction of the lens section, and
a reflection layer disposed to be opposed to the diffraction element with the channel interposed therebetween,
of the channel, at least a portion opposed to the diffraction element has a prism shape, and
the measurement method further includes detecting the diffracted-reflected light diffracted by the diffraction element, refracted by the portion having the prism shape of the channel, transmitted by the tears accumulated in the one or plurality of structure portions, and reflected by the reflection layer, of the light emitted toward the tears accumulated in the one or plurality of structure portions.

* * * * *